(12) United States Patent
Amadio et al.

(10) Patent No.: US 8,216,148 B2
(45) Date of Patent: Jul. 10, 2012

(54) DOPPLER ULTRASOUND FOR IDENTIFYING MATERIAL PROPERTIES OF A CARPAL TUNNEL ANATOMY

(75) Inventors: Peter C. Amadio, Rochester, MN (US); Chunfeng Zhao, Rochester, MN (US); Kai-Nan An, Rochester, MN (US); Marek Belohlavek, Rochester, MN (US); Mark E. Zobitz, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 1407 days.

(21) Appl. No.: 11/772,706

(22) Filed: Jul. 2, 2007

(65) Prior Publication Data
US 2008/0009736 A1    Jan. 10, 2008

Related U.S. Application Data

(60) Provisional application No. 60/819,121, filed on Jul. 7, 2006.

(51) Int. Cl.
*A61B 8/00* (2006.01)
(52) U.S. Cl. ......... 600/453; 600/437; 600/438; 600/441
(58) Field of Classification Search .................. 600/437, 600/438, 441, 453; 128/922, 923
See application file for complete search history.

(56) References Cited

U.S. PATENT DOCUMENTS
2003/0171677 A1 * 9/2003 Marmarelis .................. 600/441

FOREIGN PATENT DOCUMENTS
WO    WO 00/76400    12/2000

OTHER PUBLICATIONS

Terslev, L., Doppler Ultrasound and Magnetic Resonance Imaging of Synovial Inflammation of the Hand in Rheumatoid Arthritis: A Comparative Study, Arthritis & Rheumatism, vol. 48 No. 9, pp. 2434-2441 (2003).*
Allmann et al., "MR imaging of the carpal tunnel," Eur. J. Radiol., 1997, 25:141-145.
Armstrong et al., "Some Histological Changes in Carpal Tunnel Contents and Their Biomechanical Implications," J. Occup. Med., 1984, 26(3):197-201.
Atroshi et al., "Prevalence of Carpal tunnel Syndrome in a General Population," JAMA, 1999, 281(2):153-158.
Buchberger et al., "Carpal Tunnel Syndrome: Diagnosis with High-Resolution Sonography," Am. J. Roentgenol., 1992, 159:793-798.

(Continued)

*Primary Examiner* — Brian Casler
*Assistant Examiner* — Rajeev Siripurapu
(74) *Attorney, Agent, or Firm* — Fish & Richardson P.C.

(57) ABSTRACT

This disclosure describes methods for detecting early stages of disease, in particular carpal tunnel syndrome, by using cooperative ultrasound techniques. In a particular embodiment, a grayscale ultrasonogram may be used to detect local anatomical features within the carpal tunnel by physically moving a tendon and identifying the corresponding feature on the ultrasonogram display device. A high-resolution color Doppler ultrasound device may then be used to interrogate features of anatomy surrounding the tendon for disease. In a particular embodiment, the color Doppler ultrasound device may be used to measure the velocities of the tendon and surrounding anatomy, in particular the sub-synovial connective tissue; the resultant data may be used to quantify certain anatomical anomalies, indicative or non-indicative of carpal tunnel syndrome.

20 Claims, 9 Drawing Sheets

OTHER PUBLICATIONS

Buchberger, "Radiologic imaging of the carpal tunnel," *Eur. J. Radiol.*, 1997, 25:112-117.
Buyruk et al., "Colour doppler ultrasound examination of hand tendon pathologies. A preliminary report," *J. Hand Surg.*, 1996, 21:469-473.
Buyruk et al., "Tendon excursion measurements with colour doppler imaging. A calibration study on an embalmed human specimen," *J. Hand Surg.*, 1998, 23:350-353.
Cigali et al., "Measurement of tendon excursion velocity with colour Doppler imaging: a preliminary study on flexor pollicis longus muscle," *Eur. J. Radiol.*, 1996, 23:217-221.
de Krom et al., "Carpal tunnel syndrome: prevalence in the general population," *J. Clin. Epidemiol.*, 1992, 45(4):373-376.
Diao et al., "Carpal tunnel pressure alters median nerve function in a dose-dependent manner: a rabbit model for carpal tunnel syndrome," *J. Orthop. Res.*, 2005, 23:218-223.
Dilley et al., "The use of cross-correlation analysis between high-frequency ultrasound images to measure longitudinal median nerve movement," *Ultrasound Med. Biol.*, 2001, 27(9):1211-1218.
Duncan et al., "Sonography in the Diagnosis of Carpal Tunnel Syndrome," *Am. J. Roentgenol.*, 1999, 173:681-684.
Erel et al., "Longitudinal sliding of the median nerve in patients with carpal tunnel syndrome," *J. Hand Surg.*, 2003, 28:439-443.
Ettema et al., "A histological and immunohistochemical study of the subsynovial connective tissue in idiopathic carpal tunnel syndrome," *J. Bone Joint Surg.*, 2004, 86-A:1458-1466.
Ettema et al., "Changes in the Functional Structure of the Tenosynovium in Idiopathic Carpal Tunnel Syndrome: A Scanning Electron Microscope Study," *Plast. Reconstr. Surg.*, 2006, 118:1413-1422.
Ferrari et al., "High resolution sonography of the carpal tunnel syndrome," *Radiol. Med.*, 1997, 93:336-341 (w/English summary).
Gassner et al., "Persistent Median Artery in the Carpal Tunnel. Color Doppler Ultrasonographic Findings," *J. Ultrasound Med.*, 2002, 21:455-461.
Gelberman et al., "Intercalary flexor tendon grafts. A morphological study of intrasynovial and extrasynovial donor tendons," *Scand. J. Plast. Reconstr. Surg. Hand Surg.*, 1992, 26:257-264.
Gelberman et al., "The Carpal Tunnel Syndrome. A study of carpal canal pressures," *J. Bone Joint Surg.*, 1981, 63:380-383.
Gelberman et al., "Tissue Pressure Threshold for Peripheral Nerve Viability," *Clin. Ortho..Relat. Res.*, 1983, 178:285-291.
Greening et al., "The use of ultrasound imaging to demonstrate reduced movement of the median nerve during wrist flexion in patients with non-specific arm pain," *J. Hand Surg.*, 2001, 26:401-406.
Hirsh et al., "Chronic Tenosynovitis of the Tibialis Posterior Tendon and the Use of Tenography," *J. Foot Surg.*, 1988, 27:306-309.
Kamolz et al., "The precision of ultrasound imaging and its relevance for carpal tunnel syndrome," *Surg. Radiol. Anat.*, 2001, 23:117-121.
Keon-Cohen, "De Quervain's Disease," *J. Bone Joint Surg.*, 1951, 33-B:96-99.
Ketchum, "A Comparison of Flexor Tenosynovectomy, Open Carpal Tunnel Release, and Open Carpal Tunnel Release with Flexor Tenosynovectomy in the Treatment of Carpal Tunnel Syndrome," *Plast. Reconstr. Surg.*, 2004, 113:2020-2029.
Kraushaar and Nirschl, "Tendinosis of the Elbow (Tennis Elbow). Clinical features and findings of histological, immunohistochemical, and electron microscopy studies," *J. Bone Joint Surg.*, 1999, 81A:259-278.
Kühnel et al., "A morphological study of the peri- and epineurium in the compression zone of the median nerve in carpal tunnel syndrome," *Acta Anat.*, 1987, 129:81-91 (w/English summary).
Kutsumi et al., "Gliding resistance of the extensor pollicis brevis tendon and abductor pollicis longus tendon within the first dorsal compartment in fixed wrist positions," *J. Orthop. Res.*, 2005, 23:243-248.
LaBan et al., ""Tethered" Median Nerve Stress Test in Chronic Carpal Tunnel Syndrome," *Arch. Phys. Med. Rehabil.*, 1986, 67:803-804.
Lee et al., "Correlation of High-Resolution Ultrasonographic Findings With the Clinical Symptoms and Electrodiagnostic Data in Carpal Tunnel Syndrome," *Ann. Plast. Surg.*, 2005, 54:20-23.
Lee et al., "Diagnosis of carpal tunnel syndrome. Ultrasound versus electromyography," *Radiol. Clin. North Am.*, 1999, 37(4):859-872.
Leonard et al., "Carpal tunnel syndrome—is high-frequency ultrasound a useful diagnostic tool?," *J. Hand Surg.*, 2003, 28:77-79.
Lipscomb, "Stenosing tenosynovitis at the radial styloid process (de Quervain's disease)," *Ann. Surg.*, 1951, 134:110-115.
Lluch, "Thickening of the synovium of the digital flexor tendons: cause or consequence of the carpal tunnel syndrome?" *J. Hand Surg.*, 1992, 17:209-212.
Middleton et al., "Hand and Wrist Sonography," *Ultrasound Q.*, 2001, 17:21-36.
Missere, "Echography and the carpal tunnel syndrome," *Radiol. Med.*, 1997, 94(3):274 (w/English translation).
Moore, "Flexor Tendon Entrapment of the Digits (Trigger Finger and Trigger Thumb)," *J. Occup. Environ. Med.*, 2000, 42(5):526-545.
Nakamichi and Tachibana, "The use of ultrasonography in detection of synovitis in carpal tunnel syndrome," *J. Hand Surg.*, 1993, 18:176-179.
Nakamichi and Tachibana, "Enlarged median nerve in idiopathic carpal tunnel syndrome," *Muscle Nerve*, 2000, 23:1713-1718.
Nakamichi and Tachibana, "Histology of the Transverse Carpal Ligament and Flexor Tenosynovium in Idiopathic Carpal Tunnel Syndrome," *J. Hand Surg.*, 1998, 23:1015-1024.
Nakamichi and Tachibana, "Restricted motion of the median nerve in carpal tunnel syndrome," *J. Hand Surg.*, 1995, 20:460-464.
Nakamichi and Tachibana, "Ultrasonographic measurement of median nerve cross-sectional area in idiopathic carpal tunnel syndrome: Diagnostic accuracy," *Muscle Nerve*, 2002, 26:798-803.
Neal et al., "Pathology of the flexor tendon sheath in the spontaneous carpal tunnel syndrome," *J. Hand Surg.*, 1987, 12:229-232.
Phalen, "The Carpal-Tunnel Syndrome. Seventeen years' experience in diagnosis and treatment of six hundred fifty-four hands," *J. Bone Joint Surg.*, 1966, 48:211-228.
Regan et al., "Microscopic histopathology of chronic refractory lateral epicondylitis," *Am. J. Sports Med.*, 1992, 20(6):746-749.
Sanz et al., "Postoperative changes of carpal canal pressure in carpal tunnel syndrome: a prospective study with follow-up of 1 year," *J. Hand Surg.*, 2005, 30(6):611-614.
Sarría et al., "Carpal tunnel syndrome: usefulness of sonography," *Eur. Radiol.*, 2000, 10:1920-1925.
Schuind, "Canal Pressures Before, During, and After Endoscopic Release for Idiopathic Carpal Tunnel Syndrome," *J. Hand Surg.*, 2002, 27:1019-1025.
Soeters et al., "Reliability of Tendon Excursion Measurements in Patients Using a Color Doppler Imaging System," *J. Hand Surg.*, 2004, 29:581-586.
Soeters et al., "Non-invasive Measurement of Tendon Excursion with a Colour Doppler Imaging System: A Reliability Study in Healthy Subjects," *Scand. J. Plast. Reconstr. Surg. Hand Surg.*, 2004, 380:356-360.
Sud et al., "Absorptive properties of synovium harvested from the carpal tunnel," *Microsurgery*, 2002, 22:316-319.
Szabo and Chidgey, "Stress carpal tunnel pressures in patients with carpal tunnel syndrome and normal patients," *J. Hand Surg.*, 1989, 14:624-627.
Teefey et al., "Sonography of the Hand and Wrist," *Seminars in Ultrasound, CT, and MRI*, 2000, 21(3):192-204.
Valls-Solé et al., "Limited longitudinal sliding of the median nerve in patients with carpal tunnel syndrome," *Muscle Nerve*, 1995, 18:761-767.
Werner et al., "Intracarpal canal pressures: the role of finger, hand, wrist and forearm position," *Clin. Biomech.*, 1997, 12:44-51.
Wilhelm, "The Use of Ultrasound Imaging to Demonstrate Reduced Movement of the Median Nerve During Wrist Flexion in Patients With Non-Specific Arm Pain," *J. Hand Surg.*, 2001, 26B:407-408.
Wong et al., "Carpal Tunnel Syndrome: Diagnostic Usefulness of Sonography," *Radiology*, 2004, 232:93-99.
Ziswiler et al., "Diagnostic Value of Sonography in Patients With Suspected Carpal Tunnel Syndrome. A Prospective Study," *Arthritis Rheum.*, 2005, 52:304-311.

* cited by examiner

DOPPLER ULTRASOUND FOR IDENTIFYING MATERIAL PROPERTIES OF A CARPAL TUNNEL ANATOMY

CROSS REFERENCE TO RELATED APPLICATIONS

This application claims priority from U.S. Provisional Application Ser. No. 60/819,121, filed Jul. 7, 2006.

STATEMENT AS TO FEDERALLY SPONSORED RESEARCH

Funding for the work described herein was provided in part by the National Institutes of Arthritis and Musculoskeletal and Skin Diseases, grant number AR049823. The federal government has certain rights in the invention.

TECHNICAL FIELD

This disclosure relates to non-invasive anatomical imaging, and more particularly to detecting early stages of carpal tunnel syndrome using combined ultrasound techniques.

BACKGROUND

Carpal tunnel syndrome (CTS) is a common entrapment neuropathy. The most characteristic pathologic finding in CTS is non-inflammatory fibrosis and thickening of the peritendinous sub-synovial connective tissue (SSCT), which alters its motion characteristics with respect to the flexor tendon. The etiology of CTS is idiopathic in the majority of cases. While magnetic resonance imaging can identify the SSCT statically, there is currently no method to dynamically image the SSCT to determine if its function is different in individuals affected by CTS, as compared to unaffected individuals.

SUMMARY

This document discloses methods and systems for diagnosing disease. In one aspect, this document discloses a method for assessing synovial structure and function. The method includes identifying an intra-synovial biological structure of a mammal on an ultrasonogram display device while the biological structure is in motion, and quantifying anatomical structure by measuring flexion and extension velocity in relation to the biological structure velocity.

In a various implementations of the method, the biological structure may be a tendon, specifically a flexor tendon, and more specifically a human flexor digitorum superficialis tendon, and the surrounding anatomy may include sub-synovial connective tissue. The sub-synovial connective tissue may include the sub-synovial tissue of a human carpal tunnel anatomy.

In another aspect, the method may be used for characterizing a local anatomy of a carpal tunnel. The method may include displaying a view of an anatomy on a first ultrasonogram device, moving a tendon within the field of the first ultrasonogram device, identifying a region of sub-synovial connective tissue in proximity to the moving tendon within the field of the first ultrasonogram device, and quantifying anatomical features of the sub-synovial connective tissue by means of a second ultrasonogram device, the second device being a Doppler ultrasonogram device.

In various implementations of the method, the tendon may be a flexor digitorum superficialis tendon, and the moving of a tendon may comprise flexing and/or extending a finger of a hand, specifically, the finger may be a middle finger of a hand. The diagnostic space ratio may be a data set of measured ratios of tendon and sub-synovial connective tissue, wherein the data contains samples from persons with carpal tunnel syndrome, and persons without carpal tunnel syndrome.

In yet another aspect, the method may be used for non-invasively detecting the presence or absence of carpal tunnel syndrome. The method may include obtaining a view of a carpal tunnel anatomy with a first ultrasound device, moving a tendon within the field of the first ultrasonogram device, locating a sub-synovial connective tissue associated with the tendon by distinguishing the tendon from the surrounding anatomy by means of identifying an associated moving structure on the view of the ultrasound device.

Further, the method may include obtaining a view of the sub-synovial connective tissue with a Doppler ultrasound device, measuring, with the Doppler ultrasound device, a velocity of the tendon and a velocity of the sub-synovial connective tissue during movement, calculating the ratio of velocities of the tendon and the sub-synovial connective tissue, and comparing said ratio a diagnostic space coordinate of ratios exemplifying diseased and non-diseased tissue, wherein the position of the calculated ratio upon the diagnostic space coordinate determines the presence or absence of early stages of carpal tunnel syndrome.

In various implementations of the method, the movement may be performed by the mammal, or the movement may be effected by external forces. The external forces may include a system of pulleys and weights. The tendon may be a flexor digitorum superficialis tendon. Moving a tendon may include flexing and/or extending a finger of a hand, specifically the middle finger of a hand.

The diagnostic space ratio may be a data set of measured ratios of tendon and sub-synovial connective tissue, wherein the data contains samples from persons with carpal tunnel syndrome, and persons without carpal tunnel syndrome.

In yet another aspect, the method may be used for detecting the presence or absence of carpal tunnel syndrome. The method may include moving an intra-synovial tendon of a mammal within a field of a first ultrasonogram device, locating sub-synovial connective tissue associated with the tendon, by distinguishing the tendon from a surrounding anatomy by identifying an associated moving structure on the view of the ultrasound display, measuring, with a Doppler ultrasound device, velocity of the tendon and velocity of the sub-synovial connective tissue during movement of the tendon, calculating the ratio of the tendon velocity to sub-synovial connective tissue velocity, and comparing the ratio to a diagnostic space coordinate of ratios exemplifying diseased and non-diseased tissue, wherein the position of the calculated ratio upon the diagnostic space coordinate determines the presence or absence of early stages of carpal tunnel syndrome.

In various implementations of the method, the tendon may be a flexor digitorum superficialis tendon, and moving a tendon may include flexing and/or extending a finger of a hand, specifically the finger may be a middle finger of a hand. The diagnostic space ratio may be a data set of measured ratios of tendon and sub-synovial connective tissue, wherein the data contains samples from persons with carpal tunnel syndrome, and persons without carpal tunnel syndrome. The movement may be performed by the mammal, or, the movement may be effected by external forces. In this case, the external forces may include a system of pulleys and weights.

In another aspect, a system is disclosed comprising an ultrasonogram display device adapted to display an intrasynovial tendon of a mammal and a Doppler ultrasound device adapted to measure a velocity of said tendon and a velocity of a sub-synovial connective tissue associated with the tendon during movement of the tendon. A calculated ratio of the velocity of the tendon to the velocity of the sub-synovial connective tissue is compared to a diagnostic space coordinate of ratios exemplifying diseased and non-diseased tissue. A position of the calculated ratio upon the diagnostic space coordinate can determine presence or absence of carpal tunnel syndrome or indications of early stages of carpel tunnel syndrome.

The contents of this disclosure describe methods for detecting early stages of disease, in particular carpal tunnel syndrome, by using cooperative ultrasound techniques. In a particular embodiment, a grayscale ultrasonogram may be used to detect local anatomical features within the carpal tunnel by physically moving a tendon and identifying the corresponding feature on the ultrasonogram display device. A high-resolution color Doppler ultrasound device may then be used to interrogate features of anatomy surrounding the tendon for disease. In a particular embodiment, the color Doppler ultrasound device may be used to measure the velocities of the tendon and surrounding anatomy, in particular the sub-synovial connective tissue; the resultant data may be used to quantify certain anatomical anomalies indicative of carpal tunnel syndrome.

Unless otherwise defined, all technical and scientific terms used herein have the same meaning as commonly understood by one of ordinary skill in the art to which this disclosure pertains. Although methods and materials similar or equivalent to those described herein can be used to practice the disclosed methods, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments are set forth in the accompanying drawings and the description below. Other features, objects, and advantages will be apparent from the description and drawings, and from the claims.

DESCRIPTION OF DRAWINGS

Like reference symbols in the various drawings indicate like elements.

DETAILED DESCRIPTION

Figure 1:
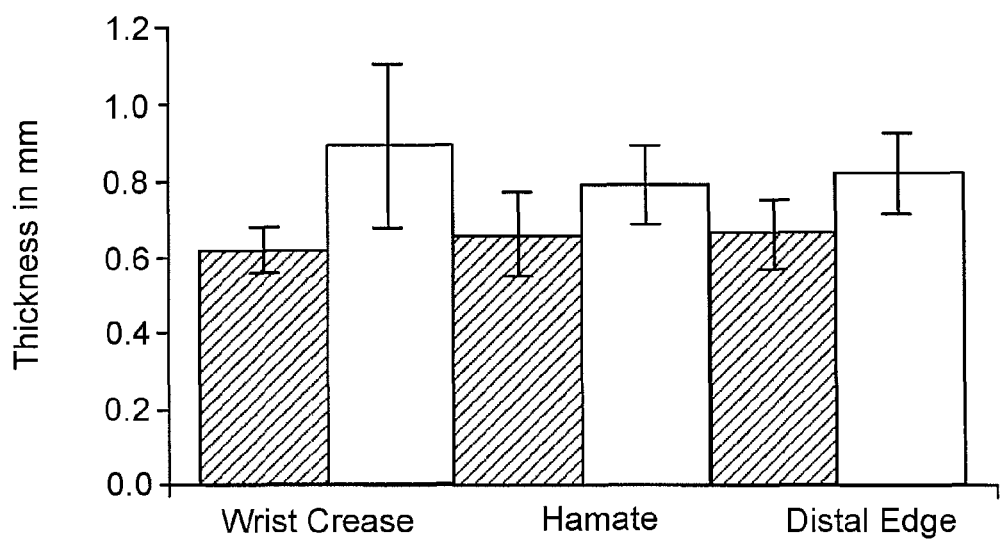
FIG. 1 is a chart showing mean thickness (±SD) of the SSCT measured with ultrasound and after dissection.

This document describes methods for non-invasively assessing anatomical features using tandem, or cooperative ultrasound techniques. In a particular embodiment, high-resolution grayscale ultrasound can be used to visualize the sub-synovial connective tissue (SSCT) in relation to a flexor digitorum superficialis (FDS) tendon, to qualitatively characterize local anatomy (including carpal ligament, median nerve, SSCT and tendon), and to analyze the SSCT thickness. Further, SSCT motion may be quantitatively analyzed with Doppler ultrasound by measuring its peak flexion and extension velocity in relation to the middle finger FDS tendon velocity. The ratio of measured velocity between the tendon and the SSCT as measured by Doppler ultrasound in a patient may be used to quantify varying degrees, or the absence of, carpal tunnel syndrome when the measured velocity is compared with a data set of similarly-measured velocities of known, diseased anatomies.

Ultrasound (also referred to as medical sonography or ultrasonography) is a commonly used noninvasive imaging modality used to visualize muscles, tendons, and other anatomies within a body. An ultrasound display device can provide views that may be used to perform diagnoses or therapeutic procedures at minimal risk to a patient or subject. Sonography can be enhanced by incorporating Doppler measurements to assess the relative movement of structures moving away from, or toward the probe, and the relative velocity of the structure. Doppler information can be displayed graphically on a display device, such as by utilizing a spectral Doppler, or as an image, using, for example, a color Doppler (directional Doppler) or power Doppler (non-directional Doppler).

The middle finger FDS tendon was chosen as representative because it is usually the most superficial of the flexor tendons in the carpal tunnel, and therefore most accessible to ultrasound; it moves most directly against the carpal flexor retinaculum during finger or wrist motion; it is adjacent to the median nerve within the carpal tunnel; and finally, because it is not encumbered by lumbrical muscle attachment or a common muscle belly with other tendons.

A diagnostic space coordinate chart can be a representation (e.g., a chart, graph, or similar means of expressing data) of ratios of tendon and SSCT velocities in a population, measured using methods such as those described above. The population may include individuals, living or dead, in which varying degrees of carpal tunnel syndrome may be present or absent. The diagnostic space coordinate chart can be referenced in comparing the measured ratio of tendon and SSCT velocities in a subject to that of the population, whereupon varying levels of disease, including absence of disease, may be inferred.

Within the carpal tunnel are the flexor digitorum profundus (FDP) and FDS tendons to each finger; the flexor pollicis longus (FPL) tendon, the tenosynovium, two bursae, the radial one for the FPL and the ulnar one for the other tendons; and the median nerve. The SSCT lies between the flexor tendons and the visceral synovium of the ulnar tenosynovial bursa (Guimberteau, 2001). The SSCT is an anatomic feature which is unique to the tendons in the carpal tunnel.

The intrasynovial tendons of the hands and feet have parietal synovial (PS) and visceral synovial (VS) sheets that form a closed space containing synovial fluid for lubrication. In extra-synovial tendons, such as the Achilles tendon, there is a peritendinous sheet of paratenon, composed of loose fibrillar tissue, which functions as an elastic sleeve, permitting free movement of the tendon against the surrounding tissue (Gelberman et al., 1992). Guimberteau has stated (Guimberteau, 2001), but without any peer-reviewed observations, that the structure of the flexor tenosynovial organization within the carpal tunnel is a hybrid of these two mechanisms, involving both paratenon (the SSCT) and synovial mechanisms.

The underlying disease mechanism for CTS is increased carpal tunnel pressure (Diao et al., 2005; Gelberman et al., 1981; Gelberman et al., 1983; Sanz et al., 2005; Schuind, 2002; Szabo and Chidgey, 1989; Werner et al., 1997). The carpal tunnel pressure can be increased, as a result of either a reduction in the size of the space in the carpal tunnel or an increase in the volume of its contents. The latter is thought to be a main factor as the most common pathological finding in CTS is non-inflammatory fibrosis and thickening of the synovium (Armstrong et al., 1984; Ettema et al., 2004; Lluch, 1992; Nakamichi and Tachibana, 1998; Neal et al., 1987; Phalen, 1966). Any condition that increases the volume of the contents of the carpal tunnel tends to compress the median nerve (Phalen, 1966). Although there are many diseases that are associated with carpal tunnel syndrome, in most cases the etiology is idiopathic.

Fibrotic changes in the tenosynovium are also noted in such conditions as de Quervain's syndrome (Keon-Cohen, 1951; Kutsumi et al., 2005; Lipscomb, 1951), trigger finger (Moore, 2000), lateral epicondylitis (Kraushaar and Nirschl, 1999; Regan et al., 1992), and tibialis posterior tendon dysfunction (Hirsh et al., 1988). How this fibrosis might affect tendon function, if at all, is unknown. In the carpal tunnel, such changes may affect nerve function, as the median nerve is often found to be tethered to the thickened SSCT in patients operated on for carpal tunnel syndrome (Allmann et al., 1997; Erel et al., 2003; Kuhnel et al., 1987; LaBan et al., 1986; Nakamichi and Tachibana, 1995; Valls-Sole et al., 1995).

High-resolution ultrasonography with high frequency (>10 MHz) transducers has been shown to be suitable for real-time assessment of dynamic changes of the median nerve in the carpal tunnel with finger flexion and extension and wrist movements (Buchberger, 1997; Sarria, 2000; Dilley, 2001) and comparable in carpal tunnel image quality to magnetic resonance imaging and computed tomography.

The use of diagnostic ultrasonography has led to enhanced ability to diagnose injuries of tendons and tendon sheaths that were previously either unrecognized or poorly understood. The usefulness of ultrasonography in monitoring carpal tunnel syndrome has also been investigated by many authors (Kamolz, 2001; Leonard L, et al., 2003; Nakamichi K, Tachibana S, 2002; Nakamichi K, Tachibana S, 1993; Sarria L, et al., 2000; Wong S M, et al., 2004; Ziswiler H R, et al., 2005). Ultrasound imaging has been described to detect pathologies such as thickening of the flexor tendons and transverse carpal ligament (Ferrari F S, et al., 1997), shape and echogenicity alterations, restricted median nerve sliding in the carpal tunnel (Erel E, et al., 2003; Greening J, et al., 2001), synovial proliferation, soft tissue infection and joint effusion, tissue calcification and tumors (Middleton W D, 2001), persistent median artery (Gassner E M, et al., 2002), tendinous and ligamentous injuries and swelling of the median nerve in the proximal part of the carpal tunnel, and flattening of the median nerve in the distal part of the carpal tunnel (Buchberger W, et al., 1992; Duncan I, et al., 1999; Ferrari F S, et al., 1997; Lee C H, et al., 2005; Wong S M, et al., 2004).

Color Doppler imaging systems are used mainly for blood flow measurements, but have also been used to assess tendon velocity and excursion in the hand and wrist region (Buyruk H M, et al., 1996; Cigali B S, et al., 1996; Soeters J N, et al., 2004). Thus, ultrasound offers the possibility of investigating synovial structure and function non-invasively. This offers an intriguing possibility for patients with CTS, as some investigators (Ettema A M, et al., 2004; Lluch A L 1992; Sud V, et al., 2002) have suggested that fibrosis of the SSCT may be a cause, and not merely an effect, of carpal tunnel syndrome. If this were so, then a method to detect changes in SSCT morphology or function might be a useful adjunct to the ultrasonic evaluation of patients with CTS. For example, changes in SSCT morphology or function could be correlated with the known ultrasonographic changes in median nerve morphology, such as nerve enlargement and/or flattening, seen in patients with carpal tunnel syndrome.

Besides its established use in cardiovascular research and clinical practice, CDI has been shown suitable for measuring tendon excursion and velocity (Cigali, 1996; Buyruk, 1998; Holland, 1999; Soeters, 2004; Soeters, 2004). Cigali et al. (Cigali, 1996) applied CDI to detect the velocity and excursion of the flexor pollicis longus tendon. The maximum tendon velocity that Cigali et al. were able to record was approximately 10 cm/sec and the same velocity value as a practical upper limit was assumed.

Non-invasive assessment of the thickness and velocity of the tenosynovium in carpal tunnel syndrome by high-resolution sonography can be used to diagnose disorders affecting the SSCT, especially carpal tunnel syndrome, as the following examples illustrate.

Example 1

Materials and Methods

The active tendon and VS gliding motion were monitored in 3 patients with carpal tunnel syndrome during carpal tunnel release surgery and compared with the corresponding simulated active tendon and VS motion in 3 cadaver controls. The motion of the middle superficial flexor tendon (FDS III) and its SSCT in the carpal tunnel, as compared to a reference point, the flexor retinaculum, were examined during finger movement with the wrist in neutral position and in neutral alignment. The flexion movement monitored was from 0° extension position to maximum individual flexion position.

The middle finger superficialis tendon was measured because it has the longest excursion of the finger flexor tendons; it is the most palmar tendon and thus moves most directly against the carpal flexor retinaculum during finger or wrist motion; it is adjacent to the median nerve within the carpal tunnel; and finally, because it is not encumbered by lumbrical muscle attachment or a common muscle belly with other tendons.

Three patients were scheduled for open carpal tunnel release for monitoring of gliding motion. The medical records were examined to obtain demographic data such as age, gender, hand dominance, side of involvement and relevant medical history of carpal tunnel syndrome-associated conditions. The surgery was preformed under local anesthesia, with an open surgical incision extending from 2 cm proximal to the wrist crease to the mid-palm. After the flexor retinaculum was transected, the carpal tunnel was exposed by a self-retaining Weitlander retractor. A small window (approximately 3 mm diameter) was made in the visceral synovium and sub-synovial connective tissue to expose the middle finger FDS tendon. With the wrist in neutral position and the fingers passively extended to 0°, a mark was made on the middle finger FDS tendon surface with a surgical marker (Skin Markers, Devon Industries, Inc, Buffalo, N.Y.). The visceral synovium surface was marked at a level 5 mm proximal to the tendon mark. A third mark was made on the cut edge of the flexor retinaculum (parietal synovium) to serve as a reference point.

The wrist was supported on the operating table in neutral position for testing. The patients were then asked to make a first, while a video camera (Sony Digital 8® Camcorder DCR-TRV350, Sony Corporation, Japan) recorded the motion. The camera was set up perpendicular to the operating table, using a tripod with a spirit level. After the motion was recorded, the carpal tunnel operation proceeded as normally. The experimental portion of the procedure took less than five minutes per patient. A millimeter ruler was included in the camera field, so that the data measured with the camcorder could be converted into a distance figure. The data was digitized with the use of Analyze Software (Biomedical Imaging Resource, Mayo Clinic, Rochester, Minn.) to determine the motion characteristics of the three marks. Any changes in the x and y axis of the digitized values of the reference point were passed on in the calculations of the other 2 markers.

Three fresh frozen human cadaver upper extremities, amputated approximately 15 cm proximal to the wrist joint, were thawed at room temperature immediately prior to testing. A medical record review was performed on each cadaver donor, to obtain the same demographic data and to be sure the individual did not have a recorded antemortem diagnosis of CTS.

A longitudinal skin incision approximately 8 cm in length was made and the flexor retinaculum was transected to open the carpal tunnel. The flexor retinaculum and skin were fixed with stay sutures laterally and medially to expose the carpal tunnel.

A window approximately 3 mm in diameter was made in the visceral synovium and sub-synovial connective tissue to expose the middle superficial flexor tendon FDS tendon. The middle superficial flexor tendon, the visceral synovium and the flexor retinaculum (parietal synovium) were marked with a marker pen similar to the patients during surgery.

The specimen was then fixed in a custom-made mounting device, holding the wrist in the neutral position, by clamping the proximal end of the radius and ulna.

The four FDS and four FDP tendons were sutured together at the proximal end of the tendons in the maximum individual flexion position of the fingers and attached to a Dacron cord. The cord controlling the flexor tendons was then actively pulled proximally by one investigator to maximum flexion of the fingers, while the motion of the three markers (from 0° extension to maximum individual flexion) was detected by anteroposterior recording with a digital camcorder. A millimeter ruler was included in the camera field, so that the data measured with the camcorder could be converted into a distance figure. The data was digitized with the use of Analyze Software (Biomedical Imaging Resource, Mayo Clinic, Rochester, Minn.) to determine the motion characteristics of the three markers. Any changes in the x and y axis of the digitized values of the reference point were passed on in the calculations of the other 2 markers.

After the testing of each cadaver specimen, SSCT biopsies were taken and sent to the Mayo Department of Laboratory Medicine and Pathology for routine hematoxylin and eosin histopathology. Light microscopy was used to evaluate the SSCT.

Accuracy and Precision of the Testing Equipment

For motion analysis accuracy testing two marks were applied to a Dacron cord, attached one end of the cord to a pulley with a 200 gram weight and the other end to an electro-potentiometer. The electro-potentiometer was set up to move the cord 40 mm. The distance between the 2 marks on the cord were measured with a ruler, marked in 1 mm increments to use as a reference for the translation of the distance in the camera pictures.

The excursion of the 2 markers was calculated from the start point and compared with the actual movement given by the actuator (40 mm). This was repeated 5 times, with the camera in renewed setup positions and also new marks on the string, giving a total of 10 measurements for validation testing. The measurements within each repetition were highly correlated (intraclass correlation=0.88), so to evaluate the accuracy, the pairs of measurements from each repetition were averaged. All five average measurements were within 2 mm of 40 mm (4 of the 5 were within 1 mm and 3 of the 5 were within 0.5 mm); and the mean absolute difference from 40 mm was 0.62 mm. The standard error of the measurements between repetitions was 0.82 mm, indicating high precision.

Statistical Methods

The relationship between the motion of the tendon and motion of the synovium was estimated by the slope of the simple linear regression line through the series of measurements taken for each patient and control subject. Specifically, the movement of the synovium was regressed on the movement of the tendon individually for each subject.

The mean slope of the regression lines was calculated for each group (patients or cadavers), and reported with 95% confidence intervals. In addition to reporting these parameter estimates, these results were used to calculate a sample size for future studies. While the focus of the analysis was on parameter estimation, to be complete the mean slopes between the two groups were compared using a Wilcoxon rank sum test. The analysis was conducted using SAS (SAS Institute Inc., Cary, N.C.).

All results are reported as mean and 95% confidence interval unless otherwise indicated.

Results

There were two female patients and one male. The females were 61 years and 70 years of age and the male patient was 61 years of age. Both women had their left hand involved, and the man the right hand. All three patients were right hand dominant. The man had idiopathic carpal tunnel syndrome, one woman had hypothyroidism and one woman had diabetes mellitus type I. They all had severe electrodiagnostic test results.

The cadaver controls included two females and one male. The age of death of the female cadavers was 86 years and 97 years of age and that of the male cadaver was 74 years of age. None of the cadavers showed any documented carpal tunnel syndrome or carpal tunnel syndrome associated disease in their history. The synovial biopsies taken after testing of the cadaver controls were normal.

A relative difference in the motion of the tendon and the visceral synovium was observed when comparing carpal tunnel syndrome and non-carpal tunnel syndrome individuals. In the cadaver specimens, the visceral synovium moved noticeably less in comparison with the tendon motion, than did the visceral synovium in the carpal tunnel patients. This suggests that the visceral synovium is more tightly tethered to the tendon in the patients than in the cadavers. This could be the result of fibrosis in the SSCT, which is the characteristic histological finding in the SSCT of individuals with carpal tunnel syndrome (Ettema et al., 2004; Ettema et al., 2006). The total movement of the VS layer was greater than that of the cadaver controls.

The focus of this study was on parameter estimation, rather than on comparison. But, to be complete the mean slopes of the regression lines from the two groups were compared. While a statistically significant difference in the relative SSCT motion between the groups (p=0.10) was not evident, with such a small sample size, the power to detect differences was low. The mean slope of the regression lines for the patients with carpal tunnel syndrome was 0.56, 95% CI (0.39-0.73), while the control subjects had a mean slope of 0.27, 95% CI (0.05-0.49). The difference in means was 0.29 with a 95% confidence interval of (0.11-0.47). Based on this data, it was estimated that in a future study, a sample of 8 patients and 8 controls would provide 90% power to detect a difference in mean slopes equal to 0.29, which would be considered to be potentially clinically significant.

Example 2

Materials and Methods

The active gliding motion of the middle superficial flexor tendon (FDS III) and SSCT in 8 patients were measured with CTS undergoing carpal tunnel release surgery (CTR) and compared these with simulated flexion in 8 cadavers with an antemortem history of CTS and in 8 cadaver controls.

The motion of the FDS III tendon and its SSCT in the carpal tunnel, as compared to a fixed reference point, the flexor retinaculum, was examined during finger movement with the wrist in neutral position and in neutral alignment. The flexion movement monitored was from 0° extension position to the maximum individual flexion position.

The middle finger superficialis tendon was measured because it has the longest excursion of the finger flexor tendons; it is the most palmar tendon and thus moves most directly against the carpal flexor retinaculum during finger or wrist motion; it is adjacent to the median nerve within the carpal tunnel; and finally, because it is not encumbered by lumbrical muscle attachment or a common muscle belly with other tendons.

Patient Selection and Preparation During Surgery

Medical records were examined to obtain demographic data such as age, gender, hand dominance, side of involvement, severity of CTS and relevant medical history of carpal tunnel syndrome-associated conditions. Patients with specific etiologies of carpal tunnel syndrome, such as diabetes, inflammatory arthritis, and wrist fracture, were excluded. The surgery was performed under local anesthesia without sedation (another exclusion factor, as it would affect cooperation), with an open surgical incision extending from 1 cm proximal to the wrist crease to the mid-palm.

After the flexor retinaculum was transected, the carpal tunnel was exposed by a self-retaining Weitlander retractor. A small window (approximately 3 mm diameter) was made in the visceral synovium and subsynovial connective tissue to expose the middle finger FDS tendon. With the wrist in neutral position and the fingers passively extended to 0°, a mark was made on the middle finger FDS tendon surface with a surgical marker (Skin Markers, Devon Industries, Inc, Buffalo, N.Y.). The visceral synovium surface was marked at a level 5 mm proximal to the tendon mark. A third mark was made on the cut edge of the flexor retinaculum to serve as a fixed reference point. The wrist was supported on the operating table in neutral position for testing.

The patients were then asked to make a first and subsequently to flex and extend the middle finger individually, while a video camera (Sony Digital 8® Camcorder DCR-TRV350, Sony Corporation, Japan) recorded the motion. The camera was set up perpendicular to the operating table, using a tripod with a spirit level. After the motion was recorded, the carpal tunnel operation proceeded as normally. The experimental portion of the procedure took less than five minutes per patient. A millimeter ruler was included in the camera field, so that the data measured with the camcorder could be converted into a distance figure. The data was digitized with the use of Analyze™ Software (Biomedical Imaging Resource, Mayo Clinic, Rochester, Minn.) to determine the motion characteristics of the three marks.

Cadaver Control Specimen Selection and Preparation

A postmortem medical record review was performed on all donors to our institution's Willed Body Program, to obtain the same demographic data as for the patients described above, and to identify eight individuals with an antemortem diagnosis of CTS and eight individuals of similar age and gender who did not have an antemortem diagnosis of CTS, or any carpal tunnel syndrome-associated conditions, such as diabetes, inflammatory arthritis, or ipsilateral wrist fracture. The sixteen fresh frozen human cadaver upper extremities so identified were amputated approximately 15 cm proximal to the wrist joint, and thawed at room temperature immediately prior to testing.

A longitudinal skin incision approximately 8 cm in length was made in the palm and distal forearm, and the flexor retinaculum was transected to open the carpal tunnel. The flexor retinaculum and skin were fixed with stay sutures laterally and medially to expose the carpal tunnel.

A window approximately 3 mm in diameter was made in the visceral synovium and subsynovial connective tissue to expose the middle finger flexor digitorum superficialis (FDS) tendon FDS. The FDS tendon, the visceral synovium and the flexor retinaculum were each marked with a marker pen similar to the patients undergoing surgery. The specimen was then fixed in a custom-made mounting device, holding the wrist in the neutral position, by clamping the proximal end of the radius and ulna.

The four FDS and four FDP tendons were sutured together at the proximal end of the tendons in the maximum individual flexion position of the fingers and attached to a Dacron cord (cord A) for simultaneous finger motion simulation. The middle finger FDS (cord B) and FDP tendons (cord C) were also separately sutured with a Dacron cord for differential finger movement testing. In this construct cord B, controlling the FDS tendon, which passed around a pulley, was actively pulled by one of the investigators while cord C, controlling the FDP tendon, passed around a pulley with a 200 g weight attached to the proximal end of the cord.

Cord A was then actively pulled proximally by one investigator to maximum flexion of the fingers, while the motion of the three markers (from 0° extension to maximum individual flexion) was detected by anteroposterior recording with a digital camcorder. After the fingers were passively extended, cord B was then actively pulled proximally by one investigator to maximum flexion, and the motion of the markers again recorded. A millimeter ruler was included in the camera field, so that the data measured with the camcorder could be converted into a distance figure. The data was digitized with the use of Analyze Software (Biomedical Imaging Resource, Mayo Clinic, Rochester, Minn.) to determine the motion characteristics of the three markers.

Statistical Methods

Demographic data was noted as mean and standard deviations. The relationship between the motion of the tendon and motion of the visceral synovium was estimated by the slope of a linear regression fit for each patient and control subject. The mean slope of the regression lines was calculated for each group, and reported with 95% confidence intervals. The mean slopes (+SD) between the two groups using a Wilcoxon rank sum test were compared. The analysis was conducted using SAS (SAS Institute Inc., Cary, N.C.). All results are reported as mean and 95% confidence interval unless otherwise indicated

Results

Patients

There were eight idiopathic carpal tunnel syndrome patients, with four left and four right hands operated on. There were six right-hand dominant and two left-hand dominant patients. The dominant hand was involved in six patients.

The mean age was 55 years (range 34-73). There were four patients with moderate, two patients with moderate-severe and two patients with severe electrophysiological results.

Cadaver Specimens with an Antemortem Diagnosis of CTS

Medical records of the patients were reviewed for demographic and medical data, and for evidence of an antemortem diagnosis of carpal tunnel syndrome. Within one year eight fresh frozen cadavers with an antemortem history of CTS were identified. There were three left and five right affected hands from six females and two males with an average age of 79 years (range 58-92). The dominant hand was right in six and left in two of these individuals. In seven cases the affected hand was the dominant one. There were five cadaver hands in which a carpal tunnel release had been done; two of these also had a biopsy of synovium taken during surgery. Of the other three hands, one had a history of having been given a single steroid injection and there were two hands in which the diagnosis had been noted by treating physicians but no treatment had been documented. In each of the cadavers which had not had carpal tunnel surgery, there was an antemortem electrodiagnostic test which confirmed the diagnosis. The severity was considered mild in each case.

Cadaver Control Specimens

Eight fresh frozen cadavers were selected as the control group. They did not have an antemortem history of CTS recorded in available medical records, nor evidence of any diseases associated with carpal tunnel syndrome. There were 3 females and 5 males with 6 right and two left hands. Hand dominance was noted only in two right-hand dominant males. The mean age was 86 years (range 78-98).

Simultaneous Digit Motion (Full Extension to Fist)

In the CTS patients and cadavers with an antemortem history of CTS, the displacement of the visceral synovial (VS) layer and surrounding soft tissue was different from the controls. One of two patterns was noted: adherence of the SSCT to the tendon, so that simultaneous or near simultaneous and synchronous motion occurred (2 patients and 1 carpal tunnel syndrome cadaver), or dissociation (6 patients and 7 carpal tunnel syndrome cadavers), and less synchronous effect on VS motion. In contrast, in all the control specimens, there was a small delay from the initiation of tendon motion until the VS began to move, after which both tendons and VS moved synchronously A mean slope of 0.14+0.08 was calculated in the 6 patients with decreased VS displacement and a mean slope of 0.22+0.13 in the 7 carpal tunnel syndrome cadaver hands decreased VS displacement. In the 8 controls the slope was 0.36+0.09. The slopes of the 6 patients and 7 cadaver hands with an antemortem CTS history had significantly lower slopes than the controls (Student-Newman-Keuls test $p<0.05$).

Isolated FDS Motion

With isolated FDS movement there was a mean slope of 0.14+0.14 in the 6 patients and in the 7 cadaver carpal tunnel syndrome hands this was 0.08+0.04. In the 8 controls the slope was 0.12+0.06.

Simultaneous Versus Single Digit Gliding

The difference of motion between isolated flexion of the FDS middle finger and making a first was compared. Comparison of differential and simultaneous motion with the inclusion of all the patients, cadaver patients and controls (N=24) shows a statistical difference of the slopes (2-tailed student T-test, $p<0.01$). For moving the fingers simultaneously a mean slope of 0.313+0.22 was found and for moving the middle finger only there was a mean slope of 0.16+0.20 (TABLE 1).

TABLE 1

Comparison of differential and simultaneous motion.

| | N | Mean (SD) Simultaneous | Mean (SD) Differential | P value |
|---|---|---|---|---|
| All | 24 | 0.313 ± 0.22 | 0.163 ± 0.20 | $P \leq 0.01$* |
| Patient | 8 | 0.269 ± 0.26 | 0.173 ± 0.15 | $P > 0.01$ |
| Cadaver patient | 8 | 0.31 + 0.29 | 0.19 + 0.33 | $0.05 < P \leq 0.1$ |
| Cadaver control | 8 | 0.36 + 0.09 | 0.12 + 0.06 | $P \leq 0.01$* |

Example 3

Methods

Cadaver Selection and Preparation

Ten upper extremities of 9 fresh frozen human cadavers, amputated approximately 15 cm proximal to the wrist joint, were thawed at room temperature immediately prior to testing.

A medical record review was performed on all cadaver donors before testing, to be sure that all individuals met the same exclusion criteria, and that the individuals did not have a reported antemortem diagnosis of carpal tunnel syndrome. Exclusion criteria included a history of diabetes, glucose intolerance, thyroid disease, rheumatoid arthritis, osteoarthrosis, degenerative joint disease, flexor tendonitis, gout, hemodialysis, BMI>30, sarcoidosis, peripheral nerve disease, amyloidosis or traumatic injuries to the ipsilateral arm.

Two cadaver hands were used to identify the anatomy of the different structural layers in the carpal tunnel (i.e. carpal ligament, ulnar bursa, SSCT and superficial flexor tendon) and also to optimize our methods for recording the velocity of the different layers within the carpal tunnel by using Doppler ultrasound. Then, these methods were tested on 8 cadaver hands without carpal tunnel syndrome.

The specimens were fixed in a custom-made mounting device, holding the wrist in the neutral position, by clamping the proximal end of the radius and ulna and with support to the dorsum of the hand. The middle finger FDS and FDP tendons were attached to a Dacron cord at the proximal end of the tendons. A 200-mg weight was attached to both cords controlling the middle finger flexor tendons. Both the cords passed around a pulley which contained an electro-potentiometer connected to a computer, for measuring the excursion (and time) of the flexor tendons during testing.

The motion of the middle finger superficial flexor tendon (FDS III) and its SSCT in the carpal tunnel were examined during finger movement with the wrist in neutral position. Motion within the carpal tunnel was induced by one investigator moving the second, third, fourth and fifth fingers of the cadaver hand together from neutral extension position to approximately 90 degrees flexion of the MCP joints.

Ultrasound Imaging System and Experimental Settings

This study was performed using the Acuson Sequoia 512® ultrasound system (Acuson Sequoia 512®, Siemens Medical Solutions, Malvern, Pa., USA), equipped with the 15L8 linear array transducer set to depth of 5 mm, and 15-MHz acquisition frequency for anatomical imaging and 8-MHz frequency during Doppler measurements. Doppler gain was typically 12 dB, 1 dynamic range 68 dB. Velocity range was set to avoid aliasing. The transducer was manually placed on the palmar wrist surface of the cadaver hand, with the wrist in neutral anatomic position. A bulk of transmission gel between transducer and wrist surface assured acoustic coupling. Scans were set to optimal depth, focus, and pulse repetition frequency (PRF). To minimize compression of the SSCT and thus its motion, the scan head was applied to the skin without additional pressure.

For analysis of local anatomy and assessment of SSCT thickness, longitudinal ultrasonograms of the middle finger superficial flexor tendon and the SSCT were obtained at three different anatomic levels; at the wrist crease (proximal tunnel); at the hook of the hamate (mid-tunnel); and at the distal edge of the flexor retinaculum (distal carpal tunnel).

For motion analysis longitudinal ultrasonograms of the middle finger superficial flexor tendon and the SSCT were obtained at the wrist crease level (proximal tunnel). This location avoided the undesirable physical contact of the flexing cadaver fingers with the transducer and allowed us to better control the angle between the ultrasound beam and the structures of interest.

Proper positioning of the transducer was assured by identifying specific anatomical structures as follows. While flexing and extending the middle finger, the middle superficial flexor tendon was first detected; because tendons are fibrillar in morphology, the flexor tendon was recognized as a moving structure with a multitude of parallel striations. Then, more palmarly, the surrounding soft tissue and the transverse ligament were identified as non-moving structures. The SSCT appeared as a thin, typically low echogenicity layer located between the flexor tendon and transverse ligament.

Localization of SSCT and Measurements of Its Thickness by Ultrasound

The localization of the SSCT was analyzed in 2 cadaver wrists with conventional grayscale ultrasound. A needle was inserted into the SSCT under ultrasound guidance. The specimen was dissected and the carpal tunnel opened to verify that the target structure was indeed the SSCT.

For measuring the SSCT thickness 5 cadaver wrists were used. The thickness was measured by placing two digital calipers on both the edges of the displayed SSCT. The ultrasound machine then calculated the distance between these two calipers. The measurements were obtained by two investigators independently, five times at each level.

After the examination with ultrasound, the 5 cadaver wrists were frozen (−80° C.). The wrists were then transversely cut at the 3 testing levels (i.e., wrist crease, hamate, and distal edge) and digitally photographed after thawing of the slices. A millimeter ruler was included for calibration. Analyze™ Software (Biomedical Imaging Resource, Mayo Clinic, Rochester, Minn.) was used to determine the thickness of the SSCT; the mean of 10 thickness measurements was obtained for each level.

Measurements of SSCT Motion by Ultrasound and Reference Electro-Potentiometer System The cadaver fingers were flexed and extended manually to achieve continuous motion of the middle finger FDS tendon. To minimize the subjectivity of the continuous manually-driven motion, two individuals were asked for assistance and blinded them from all data acquisition. Although different absolute velocities of finger motion were generated in this way and the velocities were not perfectly constant, the purpose of the study was the comparison of the velocity the SSCT with respect to that of the tendon rather than an analysis of absolute velocities.

Excursions of tendon motion were measured with the electro-potentiometer simultaneously with Doppler data acquisition by ultrasound. An event marker (electrical spike) was used to delimit, in the ultrasound machine and the electro-potentiometer system, an interval from the beginning to the end of a randomly selected series of flexions and extensions. The marked interval typically lasted for 10 to 12 flexions/extension cycles. During this interval, acquisition of velocities started by placing a Doppler gate (i.e., Doppler sampling window; approximately 1 mm long) at the SSCT level. Then, after 5-6 flexion/extension cycles, the sample was moved along the scan line onto the tendon. In this way, the same Doppler angle was maintained, and a similar number of flexion/extension cycles for the two structures were obtained.

For the purposes of this analysis, it was assumed that the tendon velocity was relatively constant between runs, and that the Doppler shift of SSCT and tendon are similar for or similar velocities, even though these tissues may differ in anisotropy.

Doppler velocity spectra corresponding to the tendon and SSCT were then obtained from 3 randomly selected flexions and extensions. Motion analysis was done directly with the ultrasound system: Doppler velocity spectra were interactively outlined and the machine calculated the peak velocity, excursion (by integrating the velocities), and duration of the movement.

At this point, tendon excursions measured with the electro-potentiometer as the reference were used and the Doppler angle cursor was adjusted until the values of the Doppler-measured excursions matched the reference. This indirect method in which excursions of the tendon measured by the electro-potentiometer were used to calibrate excursions obtained by ultrasound because the angle-correction cursor on the ultrasound system screen was virtually invisible on the complex patterns of an echogenic soft tissue background. In conventional applications of the used cardiac ultrasound system the cursor is placed on a low-echogenicity background of a blood pool. This corrected angle was then used when measuring peak velocities of the tendon and SSCT.

Statistical Analysis

Data are presented as mean±standard deviation (SD). A two-sided paired t-test was used in all analyses. SSCT thickness were compared by ultrasound to anatomical measurements. Velocity ratios of the tendon and the corresponding SSCT during both flexion and extension cycles were also compared. Differences with p values <0.05 were considered significant.

Results

SSCT Analysis

In this phase the ultrasound characteristics of the SSCT were elucidated and compared to the cadaver dissections and correlated with characteristics of normal cadaver wrists. Two fresh frozen cadaver wrists were defrosted for the testing. A needle was inserted under ultrasound guidance to mark the SSCT in a cadaver carpal tunnel. After dissection, it was verified that the correct structure, i.e., SSCT was visualized by ultrasound and the needle correctly guided.

Different layers appeared in an ultrasound longitudinal view of the carpal tunnel in a cadaveric hand view as follows. The transverse carpal ligament appeared as a gray line and the middle finger flexor tendons generated horizontal striation patterns. Between the superficial flexor tendon and the transverse ligament is the SSCT, the structure of interest. The SSCT appeared as a thin layer attached parallel to the FDS III tendon. All structures and the SSCT with its corresponding tendon in particular, became much more recognizable during motion, as they move with visibly different velocities. The bursae were not visualized in this projection. The external cortical surface of the carpal bones was well visualized at approximately 15 mm depth as a smooth bright reflection.

SSCT Thickness

Figure 2:
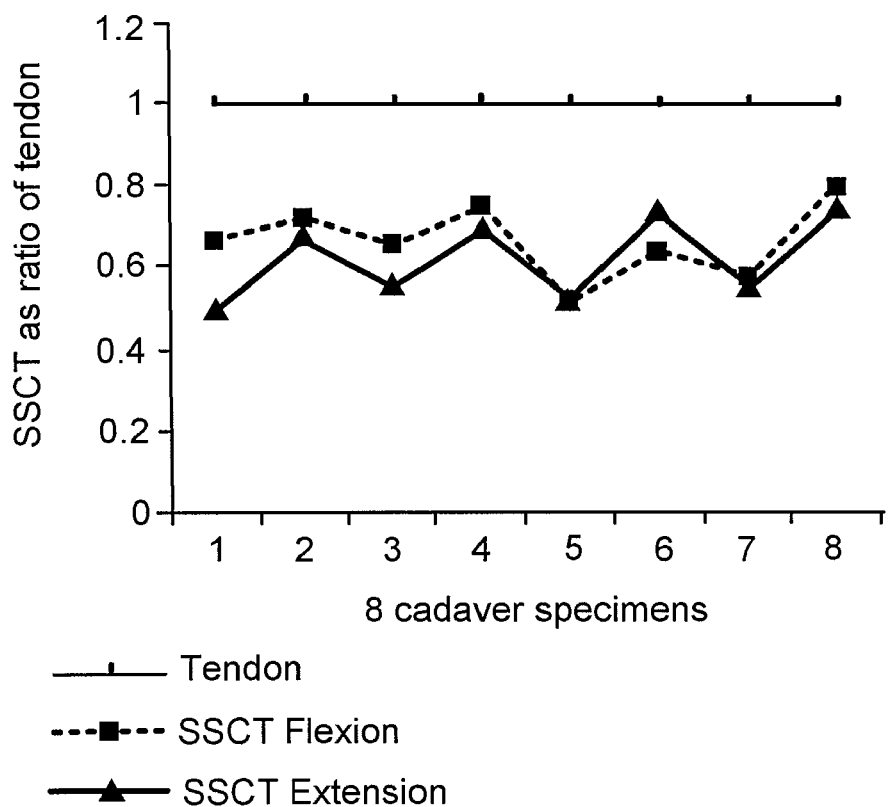
FIG. 2 is a chart showing mean peak velocities of the SSCT as a ratio of the mean peak velocities of the FDS III tendon.

For measurements of the SSCT thickness, five cadaver wrists (3 right and 2 left) from 4 cadavers (2 male, 2 female) were used with a mean age of death of 75.3 years (range 49-89 years). The comparison of the thickness of the SSCT measured with ultrasound and after anatomical dissection is shown in FIG. 2. At the wrist crease level a mean thickness of 0.62 mm (range 0.41-0.85 mm) was found, at the hamate level 0.66 mm (range 0.39-1.08 mm) and at the distal edge this was 0.66 mm (range 0.41-0.89 mm) with ultrasound. After digitizing the transverse anatomical images with the ruler, the wrist crease level measured a mean thickness of 0.89 mm (range 0.60-1.12 mm), at the hamate level 0.78 mm (range 0.51-1.02 mm) and at the distal edge this was 0.82 mm (range 0.64-0.96 mm). Although there appeared to be a small trend towards obtaining lower values of thickness with ultrasound, no statistical difference between the anatomic and ultrasound thickness measurements at these three testing levels (wrist crease p=0.12, hamate p=0.06, distal edge p=0.13) was found. Neither were any statistical difference among the ultrasound measurements or among anatomical measurements between each testing level (p>0.05) found. Finally, measurements between the two investigators were not statistically different either (p=0.49).

SSCT Motion

Eight cadaver wrists (4 right and 4 left) from 7 cadavers (3 male, 4 female) with a mean age of death of 72.4 years (range 49-89) were used.

Figure 3:
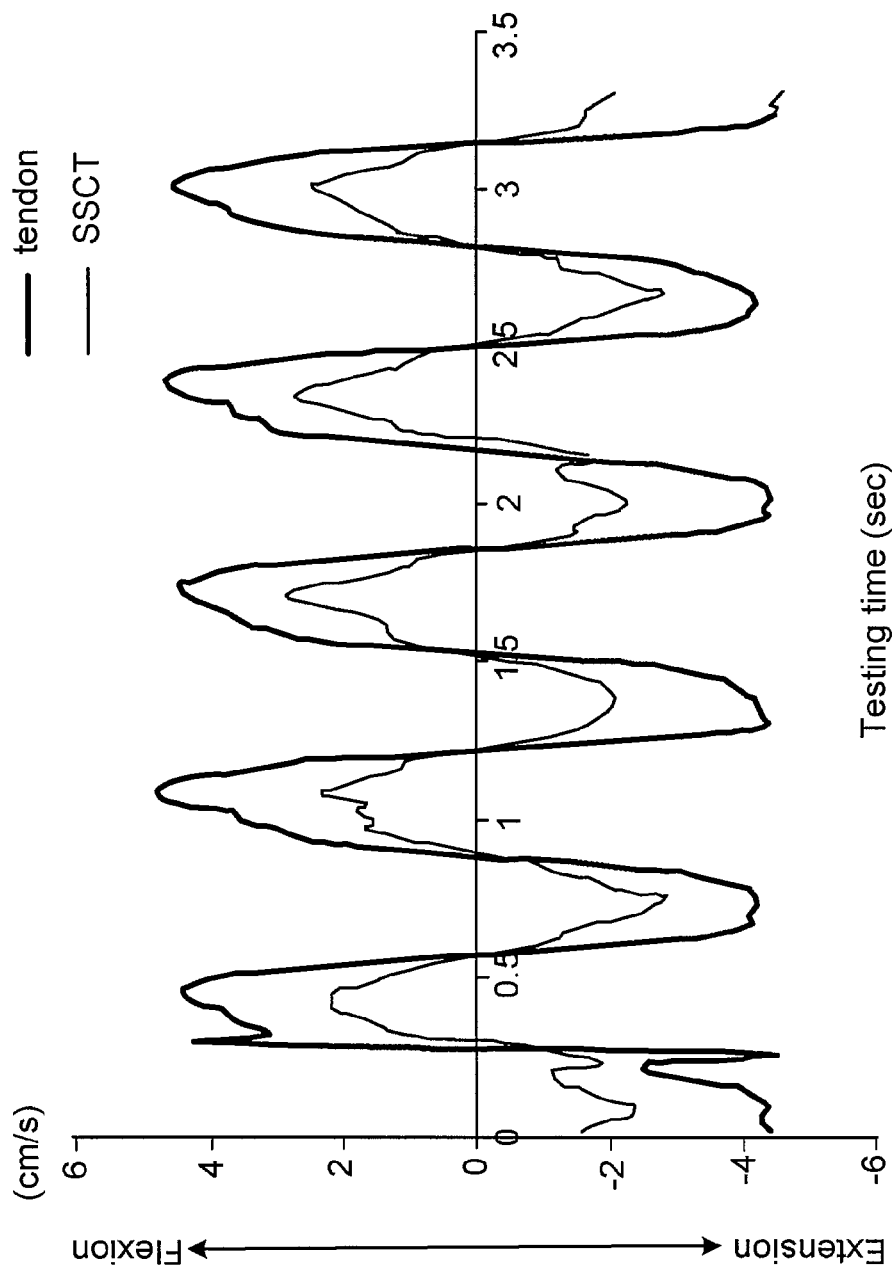
FIG. 3 is a schematic diagram of a testing device, according to one implementation.

The angle between the transducer and the tendon or SSCT was 73±8.7°. The ratio of peak flexion and extension velocities of the middle finger FDS tendon and the SSCT measured with ultrasound are shown in FIG. 3. The mean velocity of the middle FDS tendon from the 8 cadaver wrists was 14.7±7.5 cm/sec and for the SSCT this was 9.5±5.5 cm/sec during flexion movement. The mean velocity during extension movement for the middle finger FDS tendon was 14.6±7.9 and for the SSCT this was 9.3±5.0 cm/sec.

A significant difference in peak velocities for both flexion and extension motion between the tendon and the SSCT (p=0.007) was found; the velocity of the SSCT was consistently lower.

Example 4

Materials and Methods

Specimen Preparation

Six fresh frozen human upper extremities (1 bilateral and 4 unilateral), amputated approximately 15 cm proximal to the wrist joint, were obtained from 1 female and 4 male cadavers (mean age of death 82.2 years). Cadaver specimens were excluded if there was a history of carpal tunnel syndrome or other peripheral nerve disease, as well as potentially associated conditions, including diabetes or glucose intolerance, thyroid disease, rheumatoid arthritis, osteoarthritis, gout, hemodialysis, BMI>30, sarcoidosis, amyloidosis, and traumatic injuries to the ipsilateral arm. All specimens were X-rayed to exclude gross pathological evidence of injuries or major degenerative changes around the hand and wrist.

Figure 4:
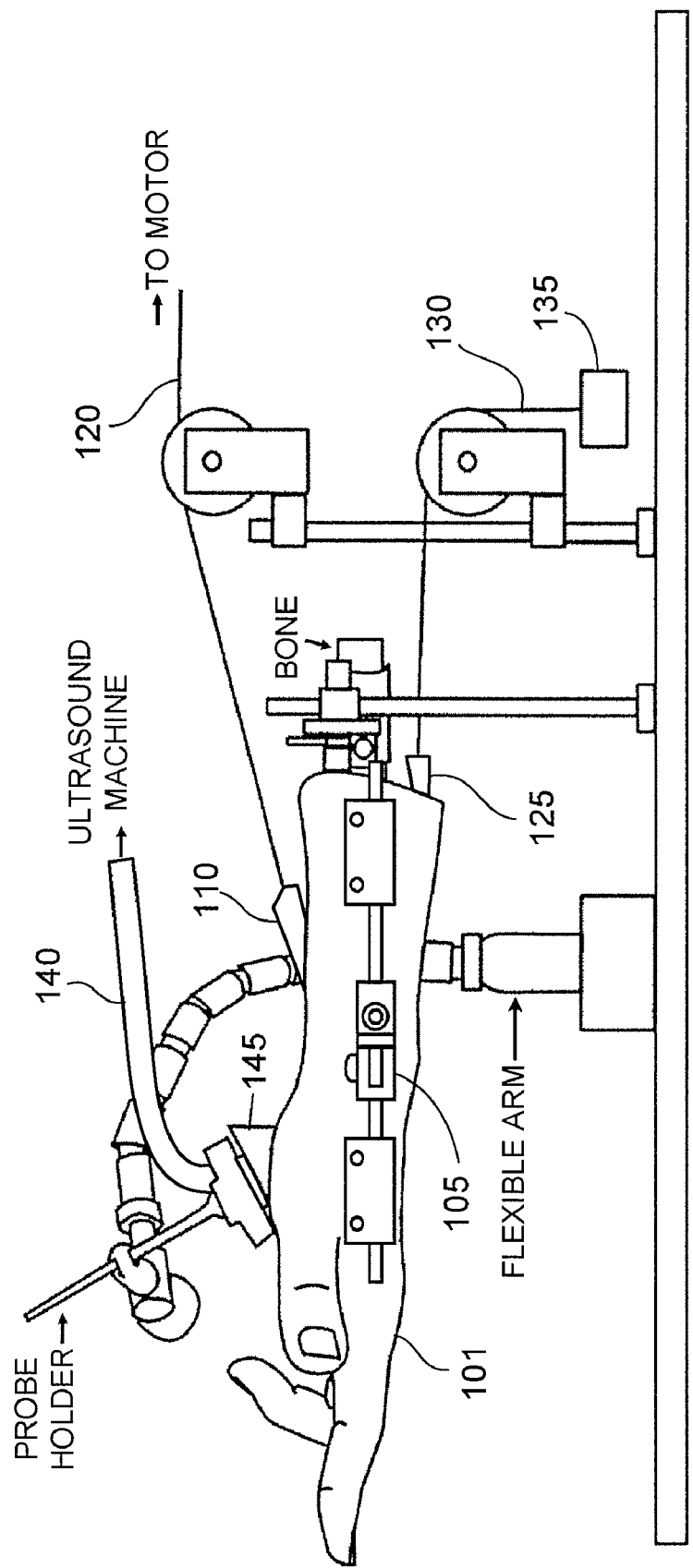
FIG. 4 is a chart showing tendon and SSCT peak velocity.

The experimental setup is shown in FIG. 4. Two screws were inserted into the index metacarpal bone at the radial side of the hand and two screws were inserted into the radial side of the distal radius. A custom made external fixator 105 with a universal joint was attached to each pair of screws, and the wrist was immobilized in the anatomical neutral position. The specimen 101 was mounted on a testing frame by clamping the proximal ends of the radius and ulna bones.

The middle finger flexor digitorum superficialis (FDS) tendon 110 was exposed in the distal forearm, and the proximal end of the tendon was connected to a stepper motor (not shown in FIG. 4) using a Dacron cord 120. The middle finger extensor digitorum tendon 125 was exposed in the distal forearm and attached to a second Dacron cord 130 connected to a 2 Newton weight 135. The excursion of the FDS was measured by noting the motion of a fixed point placed on the tendon compared to a fixed point on the fixator, as the middle finger was moved by the motor from full extension to full flexion. A "fingertip" ultrasound transducer 140 was clamped over the carpal tunnel using a custom made transducer holder attached to the mounting frame. The motor system and the specimen mounting frame were set up on separate tables to reduce any artifact which might be caused by vibration from the motor.

Tests were performed on each specimen at 4 different velocities of tendon excursion, 2.5, 5.0, 7.5 and 10.0 cm/sec. The motor excursion was set based on the previously measured middle finger FDS tendon excursion. For each test cycle, the motor pulled the FDS tendon towards the motor at the predetermined velocity until full excursion was achieved, after which the motor was reversed at the same speed, and the finger extended under the influence of the 200-gram weight attached to the extensor tendon.

Ultrasound Scanning

A Vivid 7 ultrasound scanner with a finger tip linear array 13-MHz transducer (GE Medical Systems, Milwaukee, Wis.) was used to detect motion of the middle finger FDS tendon and its corresponding SSCT. A 30-degree-wedged solid gel pad 145 (Aquaflex Gel Pad, Cone Instruments, Solon, Ohio) was put on the palmar wrist surface and then the transducer 140 was placed on the gel wedge 145, parallel to the line of the long finger FDS tendon. A small amount of liquid acoustic coupling gel was filled between the transducer 140 and wedge 145 and between the wedge 145 and skin to assure acoustical transmission.

Figure 5:
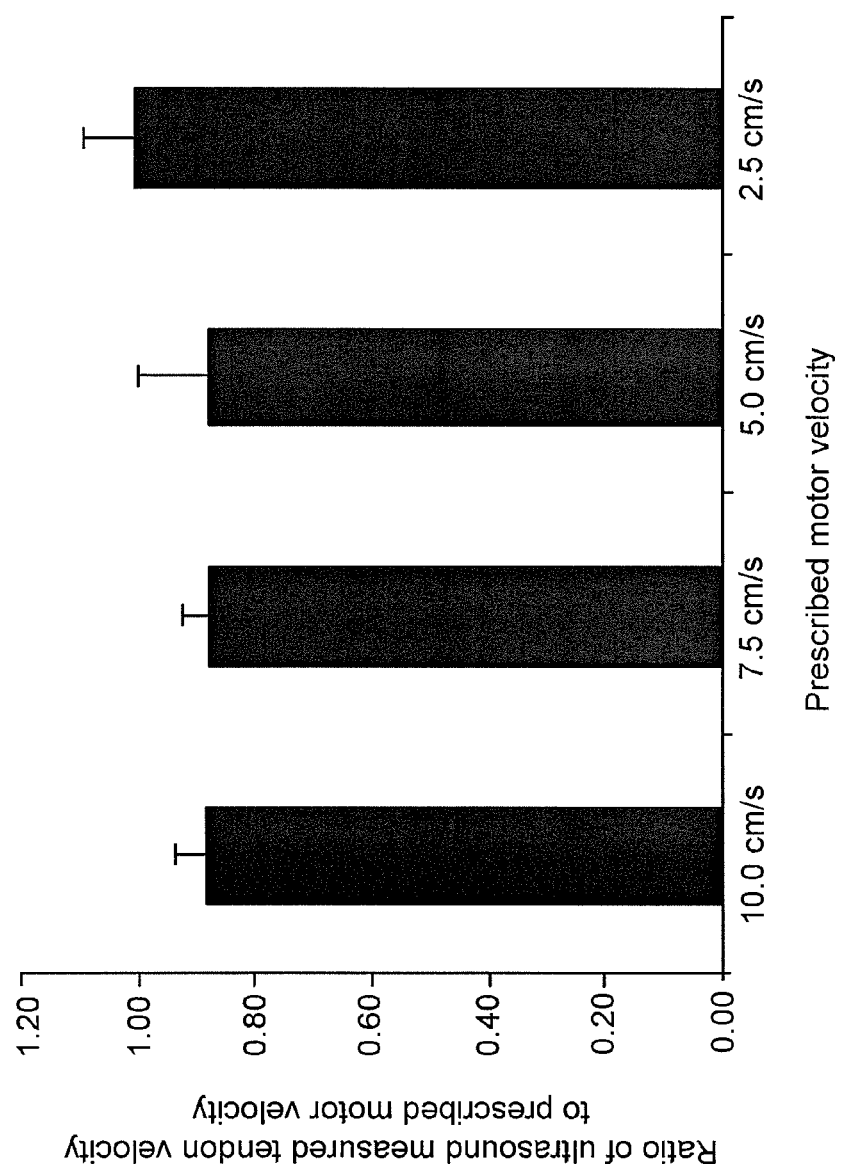
FIG. 5 is a chart of the accuracy of ultrasound measured tendon velocity to prescribed motor velocity.

The velocities of the middle finger FDS tendon and its corresponding SSCT were measured using the CDI function. Two trials of five consecutive flexion/extension movements were recorded at each motor speed for each specimen. The data were analyzed using the Q-analysis program included in the EchoPack software (GE Medical Systems, Milwaukee, Wis.). Gates 0.5 mm in diameter were used to collect velocities from the middle FDS tendon and its corresponding SSCT and the velocities in the gates were measured simultaneously. Mean peak velocity during the five finger flexion motions were considered as a velocity detected at each gate (FIG. 5).

The angle ($\theta$) between the tendon surface and the ultrasound beam on each recorded image was measured using an angle measurement algorithm programmed with Visual Basic software (Microsoft, Redmond, Wash.). The mean peak velocity for a trial was scaled using the factor $\cos \theta$ to calculate the velocity in the direction of tissue motion. The averaged data of the two trials for each motor speed were then analyzed statistically.

Statistical Analysis

The ratio of the CDI measured velocity of the middle FDS tendon to that of the stepper motor was calculated for each motor speed. The ratio of the CDI measured SSCT velocity to that of the middle FDS tendon was also compared at each prescribed motor velocity. All data were expressed as the mean±standard deviation (SD). One factor ANOVA with Tukey-Kramer post-hoc testing was used to compare the differences in the ratio of the SSCT velocity to that of the middle FDS tendon at each prescribed motor velocity. P values less than 0.05 were considered to be statistically significant.

Results

Figure 6:
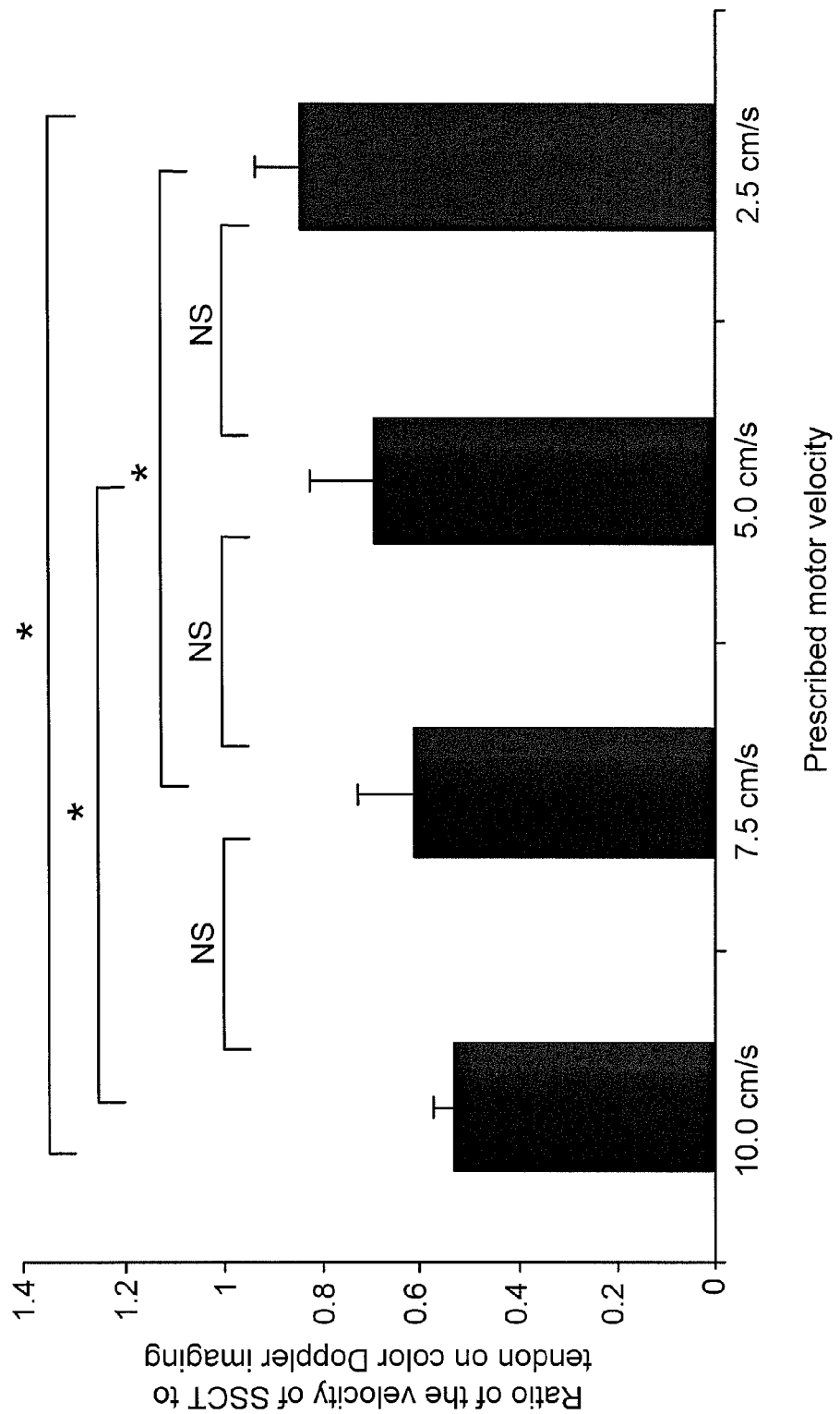
FIG. 6 is a chart of the ratio of the velocity of SSCT to the FDS tendon at the different moving velocities.

The CDI velocities of the middle FDS tendon and the SSCT were detected at 5.0, 7.5 and 10.0 cm/sec motor velocities for all the specimens. However, only 4 trials for 3 specimens were successful in detecting CDI velocities at 2.5 cm/sec motor velocity. The ratio of the CDI measured velocity of the middle FDS tendon to the motor velocity was 0.88±0.05 (n=6) at 10.0 cm/sec, 0.88±0.05 (n=6) at 7.5 cm/sec, 0.88±0.11 (n=6) at 5.0 cm/sec and 0.99±0.08 (n=3) at 2.5 cm/sec (FIG. 6).

Figure 7:
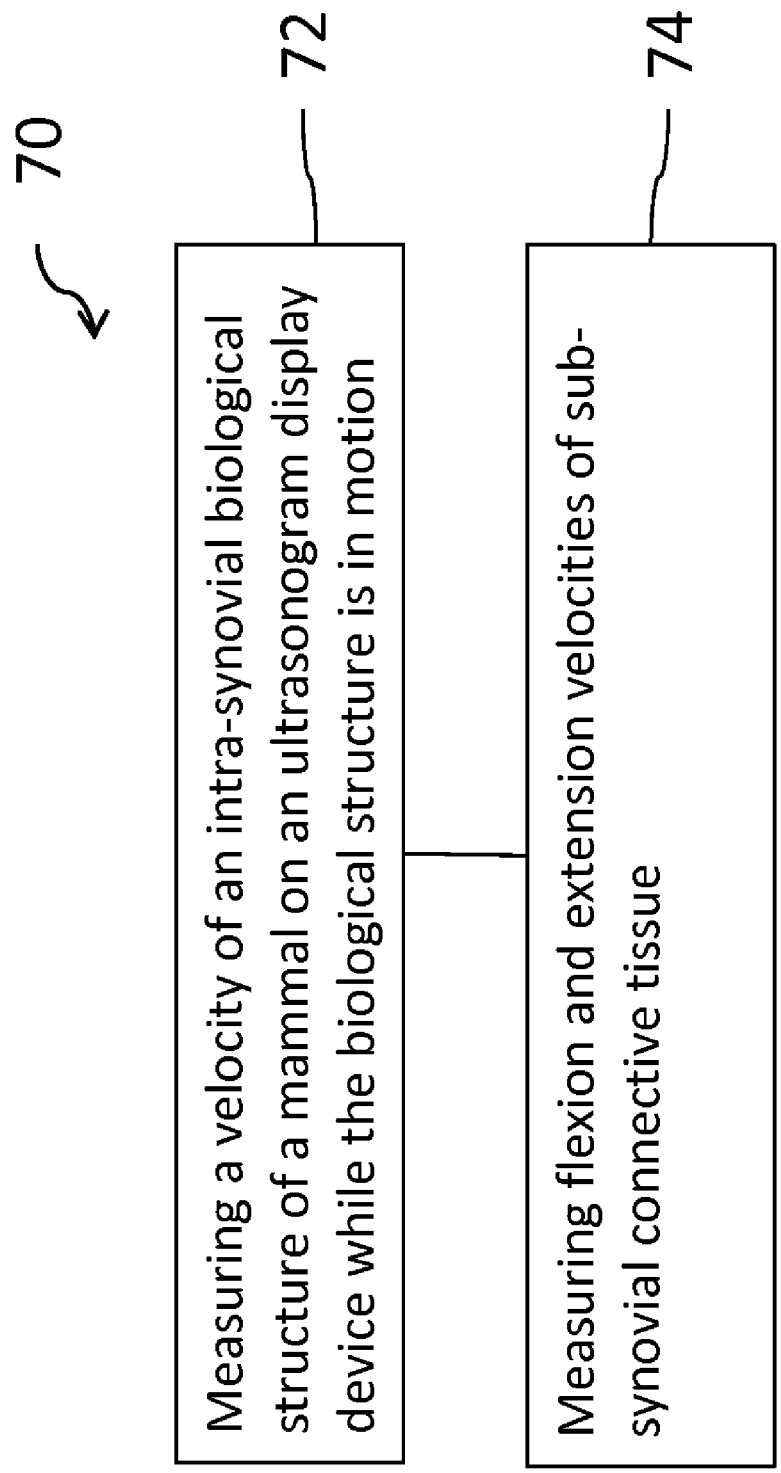
FIG. 7 is a flow chart of a method for assessing synovial structure and function according to one implementation. Method 70 can include steps 72 and 74.
Figure 8:
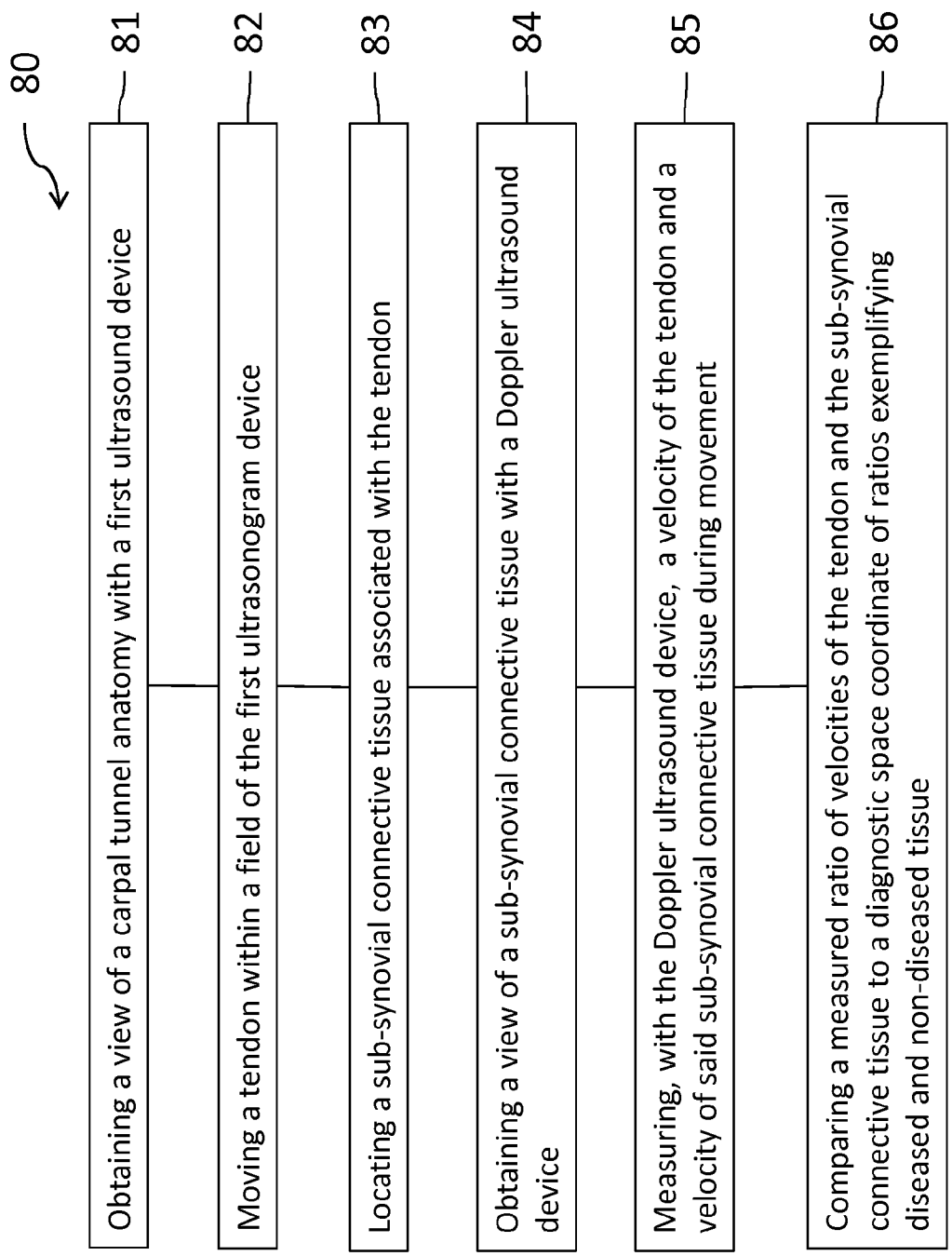
FIG. 8 is a flow chart of a method for non-invasively detecting the presence or absence of carpal tunnel syndrome according to one implementation. Method 80 can include steps 81 to 86.
Figure 9:
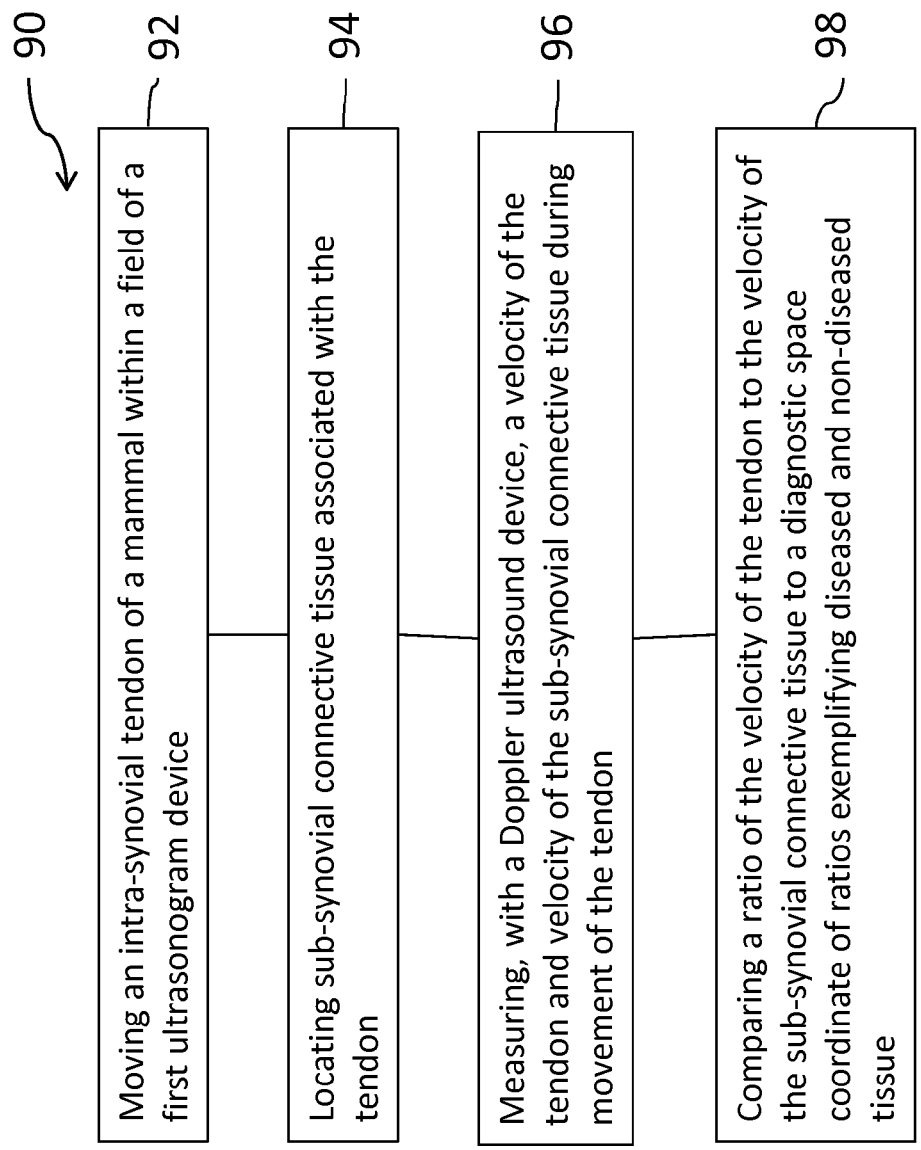
FIG. 9 is a flow chart of a method for detecting a presence or absence of carpal tunnel syndrome according to one implementation. Method 90 can include steps 92 and 94.

The ratio of the velocity of the SSCT to the middle FDS tendon was 0.53±0.04 (n=6) at 10.0 cm/sec, 0.61±0.11 (n=6) at 7.5 cm/sec, 0.69±0.13 (n=6) at 5.0 cm/sec and 0.84±0.09 (n=3) at 2.5 cm/sec. The ratio at 10 cm/sec was significantly lower than that at 5.0 and 2.5 cm/sec, and the ratio at 7.5 cm/sec was significantly lower than that at 2.5 cm/sec (FIG. 7).

A number of embodiments have been described. Nevertheless, it will be understood that various modifications may be made without departing from the spirit and scope of this disclosure. For example, adhesions around tendons or viscera could also be imaged using the principles described here. Accordingly, other embodiments are within the scope of the following claims.

REFERENCES (1) Allmann K H, Horch R, Uhl M, Gufler H, Altehoefer C, Stark G B, Langer M. 1997. MR imaging of the carpal tunnel. Eur J Radiol 25:141-145.
(2) Armstrong T J, Castelli W A, Evans F G, Diaz-Perez R. 1984. Some histological changes in carpal tunnel contents and their biomechanical implications. J Occup Med 26:197-201.
(3) Atroshi I, Gummesson C, Johnsson R, Omstein E, Ranstam J, Rosen I. 1999. Prevalence of carpal tunnel syndrome in a general population. Jama 282:153-158.
(4) de Krom M C, Knipschild P G, Kester A D, Thijs C T, Boekkooi P F, Spaans F. 1992. Carpal tunnel syndrome: prevalence in the general population. J Clin Epidemiol 45:373-376.
(5) Diao E, Shao F, Liebenberg E, Rempel D, Lotz J C. 2005. Carpal tunnel pressure alters median nerve function in a dose-dependent manner: a rabbit model for carpal tunnel syndrome. J Orthop Res 23:218-223.
(6) Erel E, Dilley A, Greening J, Morris V, Cohen B, Lynn B. 2003. Longitudinal sliding of the median nerve in patients with carpal tunnel syndrome. J Hand Surg [Br] 28:439-443.
(7) Ettema A M, Amadio P C, Zhao C, Wold L E, An K N. 2004. A histological and immunohistochemical study of the sub-synovial connective tissue in idiopathic carpal tunnel syndrome. J Bone Joint Surg Am 86-A:1458-1466.
(8) Ettema A M, Amadio P C, Zhao C, Wold L E, O'Byrne M M, Moran S L, An K-N. 2006. Changes in the functional structure of the tenosynovium in idiopathic carpal tunnel syndrome: a scanning electron microscope study. Plast Reconstr Surg: in press.
(9) Gelberman R H, Hergenroeder P T, Hargens A R, Lundborg G N, Akeson W H. 1981. The carpal tunnel syndrome. A study of carpal canal pressures. J Bone Joint Surg Am 63:380-383.
(10) Buchberger W: Radiologic imaging of the carpal tunnel. Eur J Radiol 25:112-7, 1997
(11) Buchberger W, Judmaier W, Birbamer G, et al.: Carpal tunnel syndrome: diagnosis with high-resolution sonography. AJR Am J Roentgenol 159:793-8, 1992
(12) Buyruk H M, Holland W P, Snijders C J, et al.: Tendon excursion measurements with colour Doppler imaging. J Hand Surg [Br] 23:350-3, 1998
(13) Buyruk H M, Stam H J, Lameris J S, et al.: Colour doppler ultrasound examination of hand tendon pathologies. A preliminary report. J Hand Surg [Br] 21:469-73, 1996

(14) Cigali B S, Buyruk H M, Snijders C J, et al.: Measurement of tendon excursion velocity with colour Doppler imaging: a preliminary study on flexor pollicis longus muscle. Eur J Radiol 23:217-21, 1996
(15) Dilley A, Greening J, Lynn B, et al.: The use of cross-correlation analysis between high-frequency ultrasound images to measure longitudinal median nerve movement. Ultrasound Med Biol 27:1211-8, 2001
(16) Duncan I, Sullivan P, Lomas F: Sonography in the diagnosis of carpal tunnel syndrome. AJR Am J Roentgenol 173:681-4, 1999
(17) Erel E, Dilley A, Greening J, et al.: Longitudinal sliding of the median nerve in patients with carpal tunnel syndrome. J Hand Surg [Br] 28:439-43, 2003
(18) Ettema A M, Amadio P C, Zhao C, et al.: A histological and immunohistochemical study of the sub-synovial connective tissue in idiopathic carpal tunnel syndrome. J Bone Joint Surg Am 86-A:1458-66, 2004
(19) Ferrari F S, Della Sala L, Cozza S, et al.: High-resolution ultrasonography in the study of carpal tunnel syndrome. Radiol Med (Torino) 93:336-41, 1997
(20) Gassner E M, Schocke M, Peer S, et al.: Persistent median artery in the carpal tunnel: color Doppler ultrasonographic findings. J Ultrasound Med 21:455-61, 2002
(21) Greening J, Lynn B, Leary R, et al.: The use of ultrasound imaging to demonstrate reduced movement of the median nerve during wrist flexion in patients with non-specific arm pain. J Hand Surg [Br] 26:401-6; discussion 407-8, 2001
(22) Kamolz L P, Schrogendorfer K F, Rab M, et al.: The precision of ultrasound imaging and its relevance for carpal tunnel syndrome. Surg Radiol Anat 23:117-21, 2001
(23) Ketchum L D: A comparison of flexor tenosynovectomy, open carpal tunnel release, and open carpal tunnel release with flexor tenosynovectomy in the treatment of carpal tunnel syndrome. Plast Reconstr Surg 113:2020-9, 2004
(24) Lee C H, Kim T K, Yoon E S, et al.: Correlation of High-Resolution Ultrasonographic Findings With the Clinical Symptoms and Electrodiagnostic Data in Carpal Tunnel Syndrome. Ann Plast Surg 54:20-23, 2005
(25) Lee D, van Holsbeeck M T, Janevski P K, et al.: Diagnosis of carpal tunnel syndrome. Ultrasound versus electromyography. Radiol Clin North Am 37:859-72, x, 1999
(26) Leonard L, Rangan A, Doyle G, et al.: Carpal tunnel syndrome—is high-frequency ultrasound a useful diagnostic tool? J Hand Surg [Br] 28:77-9, 2003
(27) Lluch A L: Thickening of the synovium of the digital flexor tendons: cause or consequence of the carpal tunnel syndrome? J Hand Surg [Br] 17:209-12, 1992
(28) Middleton W D, Teefey S A, Boyer M I: Hand and wrist sonography. Ultrasound Q 17:21-36, 2001
(29) Missere M: Echography and the carpal tunnel syndrome. Radiol Med (Torino) 94:274, 1997
(30) Nakamichi K, Tachibana S: Histology of the transverse carpal ligament and flexor tenosynovium in idiopathic carpal tunnel syndrome. J Hand Surg [Am] 23:1015-24, 1998
(31) Nakamichi K, Tachibana S: Ultrasonographic measurement of median nerve cross-sectional area in idiopathic carpal tunnel syndrome: Diagnostic accuracy. Muscle Nerve 26:798-803, 2002
(32) Nakamichi K, Tachibana S: The use of ultrasonography in detection of synovitis in carpal tunnel syndrome. J Hand Surg [Br] 18:176-9, 1993
(33) Nakamichi K I, Tachibana S: Enlarged median nerve in idiopathic carpal tunnel syndrome. Muscle Nerve 23:1713-8, 2000
(34) Neal N C, McManners J, Stirling G A: Pathology of the flexor tendon sheath in the spontaneous carpal tunnel syndrome. J Hand Surg [Br] 12:229-32, 1987
(35) Sarria L, Cabada T, Cozcolluela R, et al.: Carpal tunnel syndrome: usefulness of sonography. Eur Radiol 10:1920-5, 2000
(36) Soeters J N, Roebroeck M E, Holland W P, et al.: Reliability of tendon excursion measurements in patients using a color Doppler imaging system. J Hand Surg [Am] 29:581-6, 2004
(37) Sud V, Tucci M A, Freeland A E, et al.: Absorptive properties of synovium harvested from the carpal tunnel. Microsurgery 22:316-9, 2002
(38) Wong S M, Griffith J F, Hui A C, et al.: Carpal tunnel syndrome: diagnostic usefulness of sonography. Radiology 232:93-9, 2004
(39) Ziswiler H R, Reichenbach S, Vogelin E, et al.: Diagnostic value of sonography in patients with suspected carpal tunnel syndrome: a prospective study. Arthritis Rheum 52:304-11, 2005
(40) Gelberman R H, Seiler J G, 3rd, Rosenberg A E, Heyman P, Amiel D. 1992. Intercalary flexor tendon grafts. A morphological study of intrasynovial and extrasynovial donor tendons. Scand J Plast Reconstr Surg Hand Surg 26:257-264.
(41) Gelberman R H, Szabo R M, Williamson R V, Hargens A R, Yaru N C, Minteer-Convery M A. 1983. Tissue pressure threshold for peripheral nerve viability. Clin Orthop Relat Res:285-291.
(42) Guimberteau J C. 2001. New ideas in hand flexor tendon surgery. The sliding system. Vascularized flexor tendon transfers. France: Aquitaine Domaine Forestier.
(43) Hirsh S, Healey K, Feldman M. 1988. Chronic tenosynovitis of the tibialis posterior tendon and the use of tenography. J Foot Surg 27:306-309.
(44) Keon-Cohen B. 1951. De Quervain's disease. J Bone Joint Surg Br 33-B:96-99.
(45) Kraushaar B S, Nirschl R P. 1999. Tendinosis of the elbow (tennis elbow). Clinical features and findings of histological, immunohistochemical, and electron microscopy studies. J Bone Joint Surg Am 81:259-278.
(46) Kuhnel W, Schramm U, Losch G M, Schrader M. 1987. A morphological study of the peri- and epineurium in the compression zone of the median nerve in carpal tunnel syndrome. Acta Anat (Basel) 129:81-91.
(47) Kutsumi K, Amadio P C, Zhao C, Zobitz M E, An K N. 2005. Gliding resistance of the extensor pollicis brevis tendon and abductor pollicis longus tendon within the first dorsal compartment in fixed wrist positions. J Orthop Res 23:243-248.
(48) LaBan M M, Friedman N A, Zemenick G A. 1986. "Tethered" median nerve stress test in chronic carpal tunnel syndrome. Arch Phys Med Rehabil 67:803-804.
(49) Lipscomb P R. 1951. Stenosing tenosynovitis at the radial styloid process (de Quervain's disease). Ann Surg 134:110-115.
(50) Lluch A L. 1992. Thickening of the synovium of the digital flexor tendons: cause or consequence of the carpal tunnel syndrome? J Hand Surg [Br] 17:209-212.
(51) Moore J S. 2000. Flexor tendon entrapment of the digits (trigger finger and trigger thumb). J Occup Environ Med 42:526-545.
(52) Nakamichi K, Tachibana S. 1995. Restricted motion of the median nerve in carpal tunnel syndrome. J Hand Surg [Br] 20:460-464.

(53) Nakamichi K, Tachibana S. 1998. Histology of the transverse carpal ligament and flexor tenosynovium in idiopathic carpal tunnel syndrome. J Hand Surg [Am] 23:1015-1024.
(54) Neal N C, McManners J, Stirling G A. 1987. Pathology of the flexor tendon sheath in the spontaneous carpal tunnel syndrome. J Hand Surg [Br] 12:229-232.
(55) Phalen G S. 1966. The carpal-tunnel syndrome. Seventeen years' experience in diagnosis and treatment of six hundred fifty-four hands. J Bone Joint Surg Am 48:211-228.
(56) Regan W, Wold L E, Coonrad R, Morrey B F. 1992. Microscopic histopathology of chronic refractory lateral epicondylitis. Am J Sports Med 20:746-749.
(57) Sanz J, Lizaur A, Sanchez Del Campo F. 2005. Postoperative changes of carpal canal pressure in carpal tunnel syndrome: a prospective study with follow-up of 1 year. J Hand Surg [Br].
(58) Schuind F. 2002. Canal pressures before, during, and after endoscopic release for idiopathic carpal tunnel syndrome. J Hand Surg [Am] 27:1019-1025.
(59) Szabo R M, Chidgey L K. 1989. Stress carpal tunnel pressures in patients with carpal tunnel syndrome and normal patients. J Hand Surg [Am] 14:624-627.
(60) Valls-Sole J, Alvarez R, Nunez M. 1995. Limited longitudinal sliding of the median nerve in patients with carpal tunnel syndrome. Muscle Nerve 18:761-767.
(61) Werner R, Armstrong T J, Bir C, Aylard M K. 1997. Intracarpal canal pressures: the role of finger, hand, wrist and forearm position. Clin Biomech (Bristol, Avon) 12:44-51.

What is claimed is:

1. A method for non-invasively detecting the presence or absence of carpal tunnel syndrome in a mammal, comprising:
obtaining a view of a carpal tunnel anatomy with a first ultrasound device;
moving a tendon within a field of view of said first ultrasonogram device;
locating a sub-synovial connective tissue associated with said tendon;
obtaining a view of a sub-synovial connective tissue with a Doppler ultrasound device;
measuring, with the Doppler ultrasound device, a velocity of said tendon and a velocity of said sub-synovial connective tissue during movement; and
comparing a measured ratio of velocities of said tendon and said sub-synovial connective tissue to a diagnostic space coordinate of ratios exemplifying diseased and non-diseased tissue, wherein a position of the measured ratio upon said diagnostic space coordinate determines a presence or absence of early stages of carpal tunnel syndrome.

2. The method of claim 1, wherein said locating a sub-synovial connective tissue associated with said tendon is accomplished by distinguishing said tendon from surrounding anatomy by identifying an associated moving structure on said view of said ultrasound device.

3. The method of claim 1, wherein said movement is performed by said mammal.

4. The method of claim 1, wherein said movement is effected by an external force.

5. The method of claim 4, wherein said external force is generated by a system comprising a pulley and a weight.

6. The method of claim 1, wherein said tendon is a flexor digitorum superficialis tendon.

7. The method of claim 1, wherein said moving a tendon comprises flexing or extending a finger of a hand.

8. The method of claim 1, wherein said moving a tendon comprises flexing and extending a finger of a hand.

9. The method of claim 7 or 8, wherein said finger is a middle finger of said hand.

10. The method of claim 1, wherein said diagnostic space coordinate of ratios is a data set of measured ratios of tendon and sub-synovial connective tissue velocities, wherein said data contains samples from persons with carpal tunnel syndrome, and persons without carpal tunnel syndrome.

11. A method for detecting a presence or absence of carpal tunnel syndrome within a mammal, comprising:
moving an intra-synovial tendon of a mammal within a field of view of a first ultrasonogram device;
locating sub-synovial connective tissue associated with said tendon;
measuring, with a Doppler ultrasound device, a velocity of said tendon and a velocity of said sub-synovial connective tissue during movement of said tendon; and
comparing a ratio of said velocity of said tendon to said velocity of said sub-synovial connective tissue to a diagnostic space coordinate of ratios exemplifying diseased and non-diseased tissue, wherein a position of said ratio upon said diagnostic space coordinate determines a presence or absence of early stages of carpal tunnel syndrome.

12. The method of claim 11, wherein said locating sub-synovial connective tissue is accomplished by distinguishing said tendon from a surrounding anatomy by identifying an associated moving structure on a view of the ultrasound display.

13. The method of claim 11, wherein said tendon is a flexor digitorum superficialis tendon.

14. The method of claim 11, wherein said moving a tendon comprises flexing and/or extending a finger of a hand.

15. The method of claim 14, wherein said finger is a middle finger of said hand.

16. The method of claim 11, wherein said diagnostic space coordinate of ratios is a data set of measured ratios of tendon and sub-synovial connective tissue velocities, wherein said data set comprises samples from persons with carpal tunnel syndrome, and persons without carpal tunnel syndrome.

17. The method of claim 11, wherein said movement is performed by said mammal.

18. The method of claim 11, wherein said movement is effected by an external force.

19. The method of claim 18, wherein said external force is generated by a system comprising a pulley and a weight.

20. A system, comprising: an ultrasonogram device configured to display an intra-synovial tendon of a mammal; and a Doppler ultrasound device configured to measure a velocity of said tendon and a velocity of a sub-synovial connective tissue associated with said tendon during a movement of said tendon; wherein a calculated ratio of said velocity of said tendon to said velocity of said sub-synovial connective tissue is compared to a diagnostic space coordinate of ratios exemplifying diseased and non-diseased tissue, wherein a position of said calculated ratio upon the diagnostic space coordinate determines a presence or absence of carpal tunnel syndrome or indications of early stages of carpel tunnel syndrome.

* * * * *